(12) United States Patent
Epp et al.

(10) Patent No.: US 9,603,364 B2
(45) Date of Patent: Mar. 28, 2017

US009603364B2

(54) 4-AMINO-6-(HALO-SUBSTITUTED-ALKYL)-PICOLINATES AND THEIR USE AS HERBICIDES

(71) Applicant: Dow AgroSciences LLC, Indianapolis, IN (US)

(72) Inventors: Jeffrey B. Epp, Noblesville, IN (US); Lindsey G. Fischer, Indianapolis, IN (US); Jeremy Kister, Carmel, IN (US); Norbert M. Satchivi, Carmel, IN (US); Paul R. Schmitzer, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/564,192

(22) Filed: Dec. 9, 2014

(65) Prior Publication Data

US 2015/0164074 A1     Jun. 18, 2015

Related U.S. Application Data

(60) Provisional application No. 61/915,309, filed on Dec. 12, 2013.

(51) Int. Cl.
  *C07D 213/78* (2006.01)
  *A01N 43/40* (2006.01)
  *C07D 213/79* (2006.01)
  *A01N 47/20* (2006.01)

(52) U.S. Cl.
  CPC ............. *A01N 43/40* (2013.01); *A01N 47/20* (2013.01); *C07D 213/79* (2013.01)

(58) Field of Classification Search
  None
  See application file for complete search history.

(56) References Cited

U.S. PATENT DOCUMENTS 7,432,227 B2 * 10/2008 Balko et al. .................. 504/260

OTHER PUBLICATIONS

CAPLUS 1974:56246.*

* cited by examiner

*Primary Examiner* — Heidi Reese
(74) *Attorney, Agent, or Firm* — Michael J. Terapane

(57) ABSTRACT

Provided herein are 4-amino-6-(halo-substituted-alkyl)-picolinic acids and their derivatives, compositions comprising the acids and their derivatives, and methods of use thereof as herbicides.

16 Claims, No Drawings

4-AMINO-6-(HALO-SUBSTITUTED-ALKYL)-PICOLINATES AND THEIR USE AS HERBICIDES

CROSS REFERENCE TO RELATED APPLICATIONS

This application claims the benefit of U.S. Provisional Patent Application Ser. No. 61/915,309, filed Dec. 12, 2013, the disclosure of which is expressly incorporated herein by reference.

BACKGROUND

The occurrence of undesirable vegetation, e.g., weeds, is a constant problem facing farmers in crops, pasture, and other settings. Weeds compete with crops and negatively impact crop yield. The use of chemical herbicides is an important tool in controlling undesirable vegetation.

There remains a need for new chemical herbicides that offer a broader spectrum of weed control, selectivity, minimal crop damage, storage stability, ease of handling, higher activity against weeds, and/or a means to address herbicide-tolerance that develops with respect to herbicides currently in use.

SUMMARY

Provided herein are compounds of Formula (I):

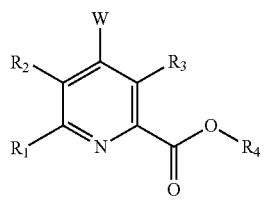

(I)

wherein
$R_1$ is $C_1$-$C_4$ alkyl or $C_1$-$C_4$ alkenyl which are optionally substituted with one or more halogen atom(s), with the proviso that $R_1$ is not 1,1-difluoroethyl or trifluoromethyl;
$R_2$ is H, Cl or F;
$R_3$ is halogen;
$R_4$ is H, $C_1$-$C_4$ alkyl or alkylaryl;
W is —$N_3$, —$NR_5R_6$, —NHOH, —$NHCOR_6$ or —N=$CR_7R_8$;
wherein
$R_5$ represents H or $C_1$-$C_4$ alkyl;
$R_6$ represents H, $C_1$-$C_4$ alkyl or $C_1$-$C_4$ alkoxy;
$R_5$ and $R_6$ taken together with N represent a 5- or 6-membered saturated or unsaturated ring which may contain additional O, S or N heteroatoms;
$R_7$ represents H or $C_1$-$C_4$ alkyl;
$R_8$ represents $C_1$-$C_4$ alkoxy or $C_1$-$C_4$ alkylamine;
or a N-oxide or agriculturally acceptable salt thereof.

Also provided herein are methods of controlling undesirable vegetation including contacting undesirable vegetation or the locus thereof with or applying to the soil or water to prevent the emergence or growth of the undesirable vegetation the compounds of Formula I provided herein.

DETAILED DESCRIPTION

As used herein, herbicide and herbicidal active ingredient mean a compound that controls undesirable vegetation when applied in an appropriate amount.

As used herein, control of or controlling undesirable vegetation means killing or preventing the vegetation, or causing some other adverse modifying effect to the vegetation e.g., deviations from natural growth or development, regulation, desiccation, retardation, and the like.

As used herein, a herbicidally effective or vegetation controlling amount is an amount of herbicidal active ingredient the application of which controls the relevant undesirable vegetation.

As used herein, applying a herbicide or herbicidal composition means delivering it directly to the targeted vegetation or to the locus thereof or to the area where control of undesired vegetation is desired. Methods of application include, but are not limited to, pre-emergently contacting soil or water, or post-emergently contacting the undesirable vegetation or area adjacent to the undesirable vegetation.

As used herein, plants and vegetation include, but are not limited to, dormant seeds, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Suitable salts include those derived from alkali or alkaline earth metals and those derived from ammonia and amines. Preferred cations include sodium, potassium, magnesium, and ammonium cations of the formula:

$R_9R_{10}R_{11}R_{12}N^+$ wherein $R_9$, $R_{10}$, $R_{11}$ and $R_{12}$ each, independently represents H or $C_1$-$C_{12}$ alkyl, $C_3$-$C_{12}$ alkenyl, or $C_3$-$C_{12}$ alkynyl, each of which is optionally substituted by one or more substituents such as hydroxy, $C_1$-$C_4$ alkoxy, $C_1$-$C_4$ alkylthio, or phenyl groups, provided that $R_9$, $R_{10}$, $R_{11}$ and $R_{12}$ are sterically compatible. Additionally, any two $R_9$, $R_{10}$, $R_{11}$ and $R_{12}$ together may represent an aliphatic difunctional moiety containing one to twelve carbon atoms and up to two oxygen or sulfur atoms. Salts of the compounds of Formula I can be prepared by treatment of compounds of Formula I with a metal hydroxide, such as sodium hydroxide, with an amine, such as ammonia, trimethylamine, diethanolamine, 2-methyl-thiopropylamine, bisallylamine, 2-butoxyethylamine, morpholine, cyclododecylamine, or benzylamine, or with a tetraalkylammonium hydroxide, such as tetramethylammonium hydroxide or choline hydroxide. Amine salts of compounds of Formula I are useful forms or derivatives of compounds of Formula I because they are water-soluble and lend themselves to the preparation of desirable aqueous based herbicidal compositions.

Other forms or derivatives of compounds of the Formula I include N-oxides of compounds of Formula I. Pyridine N-oxides can be obtained by oxidation of the corresponding pyridines. Suitable oxidation methods are described, for example, in Houben-Weyl, Methoden der organischen Chemie [Methods in organic chemistry], expanded and subsequent volumes to the 4th edition, volume E 7 b, p. 565 f.

As used herein "acyl" includes formyl, ($C_1$-$C_3$ alkyl) carbonyl, and ($C_1$-$C_3$ haloalkyl)carbonyl.

As used herein, "alkyl" refers to saturated, straight-chained or branched hydrocarbon moieties. The alkyl groups can be various lengths, e.g., $C_{1-n}$, where n is 2, 3, 4, 5, 6, 7, 8, 9, or 10. Unless otherwise specified, alkyl refers to a $C_1$-$C_{10}$ alkyl group. Examples include, but are not limited to, methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl. Alkyl groups as used herein include halo substituted alkyls which are defined below as haloalkyl groups.

As used herein, "alkylaryl" refers to straight-chained or branched alkyl groups, wherein one or more of the hydrogen atoms may be substituted with an aryl group. Aryl groups as used herein are defined below.

As used herein, "alkoxyalkyl" refers to straight-chained or branched alkyl groups, wherein these groups the hydrogen atoms may partially or entirely be substituted with one or more alkoxy substituent(s).

As used herein, "haloalkyl" refers to straight-chained or branched alkyl groups, wherein these groups the hydrogen atoms may partially or entirely be substituted with one or more halogen atom(s). The haloalkyl groups can be various lengths, e.g., $C_{1-n}$, where n is 2, 3, 4, 5, 6, 7, or 8. Unless otherwise specified, haloalkyl refers to a $C_1$-$C_8$ group. Examples include, but are not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl, and 1,1,1-trifluoroprop-2-yl.

As used herein, "alkenyl" refers to unsaturated, straight-chained, or branched hydrocarbon moieties containing one or more double bond(s). The alkenyl groups can be various lengths, e.g., $C_{1-n}$, where n is 2, 3, 4, 5, 6, 7, or 8. Unless otherwise specified, alkenyl refers to a $C_2$-$C_8$ alkenyl group. Alkenyl groups may contain more than one unsaturated bond. Examples include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl.

As used herein, "alkynyl" represents straight-chained or branched hydrocarbon moieties containing one or more triple bond(s). The alkynyl groups can be various lengths, e.g., $C_{1-n}$, where n is 2, 3, 4, 5, 6, 7, or 8. Unless otherwise specified, alkynyl refers to a $C_2$-$C_8$ alkynyl group. Alkynyl groups may contain more than one unsaturated bond. Examples include, but are not limited to, $C_2$-$C_6$-alkynyl, such as ethynyl, 1-propynyl, 2-propynyl (or propargyl), 1-butyynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butinyul, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl.

As used herein, "alkoxy" refers to a group of the formula R—O—, where R is alkyl as defined above. The alkoxy groups can be various lengths, e.g., $C_{1-n}$, where n is 2, 3, 4, 5, 6, 7, or 8. Unless otherwise specified, R is a $C_1$-$C_8$ alkyl group. Examples include, but are not limited to, methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

As used herein, "haloalkoxy" refers to a group of the formula R—O—, where R is haloalkyl as defined above. R in the haloalkoxys can be various lengths, e.g., $C_{1-n}$, where n is 2, 3, 4, 5, 6, 7, or 8. Unless otherwise specified, R is a $C_1$-$C_8$ alkyl group. Examples include, but are not limited to, chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro,2-difluoroethoxy, 2,2-dichloro-2-fluoroethoxy, 2,2,2-trichloroethoxy, pentafluoroethoxy, and 1,1,1-trifluoroprop-2-oxy.

As used herein, "alkylthio" refers to a group of the formula R—S— where R is alkyl as defined above. R in the alkylthio groups can be various lengths, e.g., $C_{1-n}$, where n is 2, 3, 4, 5, 6, 7, or 8. Unless otherwise specified, R is a $C_1$-$C_8$ alkyl group. Examples include, but are not limited to, methylthio, ethylthio, propylthio, 1-methylethylthio, butylthio, 1-methyl-propylthio, 2-methylpropylthio, 1,1-dimethylethylthio, pentylthio, 1-methylbutylthio, 2-methylbutylthio, 3-methylbutylthio, 2,2-dio-methylpropylthio, 1-ethylpropylthio, hexylthio, 1,1-dimethyl propylthio, 1,2-dimethyl propylthio, 1-methylpentylthio, 2-methylpentylthio, 3-methylpentylthio, 4-methyl-pentylthio, 1,1-dimethyl butylthio, 1,2-dimethyl-butylthio, 1,3-dimethyl-butylthio, 2,2-dimethyl butylthio, 2,3-dimethyl butylthio, 3,3-dimethylbutylthio, 1-ethylbutylthio, 2-ethylbutylthio, 1,1,2-trimethyl propylthio, 1,2,2-trimethyl propylthio, 1-ethyl-1-methyl propylthio, and 1-ethyl-2-methylpropylthio.

As used herein, "haloalkylthio" refers to an alkylthio group as defined above wherein the carbon atoms are partially or entirely substituted with one or more halogen atoms. The haloalkylthio groups can be various lengths, e.g., $C_{1-n}$, where n is 2, 3, 4, 5, 6, 7, or 8. Unless otherwise specified, haloalkylthio include a $C_1$-$C_8$ alkyl group. Examples include, but are not limited to, chloromethylthio, bromomethylthio, dichloromethylthio, trichloromethylthio, fluoromethylthio, difluoromethylthio, trifluoromethylthio, chlorofluoromethylthio, dichlorofluoro-methylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-difluoroethylthio, 2,2-dichloro-2-fluoroethylthio, 2,2,2-trichloroethylthio, pentafluoroethylthio, and 1,1,1-trifluoroprop-2-ylthio.

As used herein, "aryl," as well as derivative terms such as "aryloxy," refers to a phenyl, indanyl, or naphthyl group. In some embodiments, phenyl is preferred. The term "heteroaryl," as well as derivative terms such as "heteroaryloxy," refers to a 5- or 6-membered aromatic ring containing one or more heteroatoms, e.g., N, O or S; these heteroaromatic rings may be fused to other aromatic systems. The aryl or heteroaryl substituents may be unsubstituted or substituted with one or more substituents selected from, e.g., halogen, hydroxy, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, ($C_1$-$C_6$alkoxy)carbonyl, $C_1$-$C_6$ carbamoyl, hydroxycarbonyl, ($C_1$-$C_6$ alkyl)carbonyl, aminocarbonyl, ($C_1$-$C_6$ alkylamino)carbonyl, (di($C_1$-$C_6$alkyl)amino)carbonyl, provided that the substituents are sterically compatible and the rules of chemical bonding and strain energy are satisfied. In some embodiments, preferred substituents include, for example, halogen, $C_1$-$C_2$ alkyl, and $C_1$-$C_2$ haloalkyl.

As used herein, "alkoxycarbonyl" refers to a group of the formula

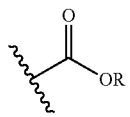

wherein R is alkyl.

As used herein, "alkylamino" or "dialkylamino" refers to an amino group substituted with one or two alkyl groups, which may be the same or different.

As used herein, "alkylcarbamyl" refers to a carbamyl group substituted on the nitrogen with an alkyl group.

As used herein, "alkylsulfonyl" refers to —SO$_2$R, wherein R is alkyl (e.g., $C_1$-$C_{10}$ alkyl).

As used herein, "carbamyl" (also referred to as carbamoyl or aminocarbonyl) refers to a group of the formula

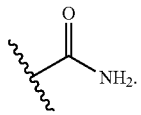 [SMILES: *C(N)=O]

As used herein, "haloalkylamino" refers to an alkylamino group wherein the alkyl carbon atoms are partially or entirely substituted with one or more halogen atoms, As used herein, "Me" refers to a methyl group.

As used herein, the term "halogen," including derivative terms such as "halo," refers to fluorine, chlorine, bromine, or iodine (or fluoride, chloride, bromide, or iodide).

As used herein, plants and vegetation include, but are not limited to, germinant seeds, emerging seedlings, plants emerging from vegetative propagules, immature vegetation, and established vegetation.

Compounds

Provided herein are compounds of Formula (I):

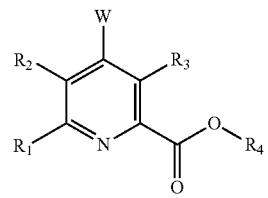

wherein $R_1$ is $C_1$-$C_4$ alkyl or $C_1$-$C_4$ alkenyl which are optionally substituted with one or more halogen atom(s), with the proviso that $R_1$ is not 1,1-difluoroethyl or trifluoromethyl;

$R_2$ is H, Cl or F;

$R_3$ is halogen;

$R_4$ is H, $C_1$-$C_4$ alkyl or alkylaryl;

W is —N$_3$, —NR$_5$R$_6$, —NHOH, —NHCOR$_6$ or —N=CR$_7$R$_8$;

wherein $R_5$ represents H or $C_1$-$C_4$ alkyl;

$R_6$ represents H, $C_1$-$C_4$ alkyl or $C_1$-$C_4$ alkoxy;

$R_5$ and $R_6$ taken together with N represent a 5- or 6-membered saturated or unsaturated ring which may contain additional O, S or N heteroatoms;

$R_7$ represents H or $C_1$-$C_4$ alkyl;

$R_8$ represents $C_1$-$C_4$ alkoxy or $C_1$-$C_4$ alkylamine;

or a N-oxide or agriculturally acceptable salt thereof.

In some embodiments, $R_1$ is a fluoro substituted $C_1$-$C_4$ alkyl, for example, but not limited to, difluoromethyl or 1-fluoroethyl. With respect to Formula I as described herein, $R_1$ is not 1,1-difluoroethyl or trifluoromethyl.

In some embodiments, $R_3$ is Cl.

In some embodiments $R_4$ is H. In other embodiments $R_4$ is CH$_3$.

In some embodiments, $R_1$ is 1-fluoroethyl, $R_2$ is H, and $R_3$ is Cl. In other embodiments, $R_1$ is difluoromethyl, $R_2$ is H, and $R_3$ is Cl.

In some embodiments, W is NH$_2$.

In some embodiments, the compound of Formula I is a N-oxide or an agriculturally acceptable salt thereof. In some embodiments, the compound of Formula I is a carboxylic acid (i.e., $R_4$ is H) or a methyl ester (i.e., $R_4$ is CH$_3$).

Compositions and Methods

In some embodiments, the compounds provided herein are employed in mixtures containing a herbicidally effective amount of the compound along with at least one agriculturally acceptable adjuvant or carrier. Exemplary adjuvants or carriers include those that are not phytotoxic or significantly phytotoxic to valuable crops, e.g., at the concentrations employed in applying the compositions for selective weed control in the presence of crops, and/or do not react or significantly react chemically with the compounds of provided herein or other composition ingredients. Such mixtures can be designed for application directly to weeds or their locus or can be concentrates or formulations that are \diluted with additional carriers and adjuvants before application. They can be solids, such as, for example, dusts, granules, water dispersible granules, or wettable powders, or liquids, such as, and for example, emulsifiable concentrates, solutions, emulsions or suspensions. They can also be provided as a pre-mix or tank-mixed.

Suitable agricultural adjuvants and carriers that are useful in preparing the herbicidal mixtures of the disclosure are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8 EO); tallow amine ethoxylate (15 EO); PEG (400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethylhexyl stearate, n-butyl oleate, isopropyl myristate, propylene glycol dioleate, di-octyl succinate, di-butyl adipate, di-octyl phthalate and the like; esters of mono-, di- and poly-carboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers, and the like. In some embodiments, water is the carrier for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

In some embodiments, one or more surface-active agents are utilized in the compositions of the present disclosure. Such surface-active agents are, in some embodiments, employed in both solid and liquid compositions, e.g., those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in *McCutcheon's Detergents and Emulsifiers Annual*, MC Publishing Corp., Ridgewood, N.J., 1998, and in *Encyclopedia of Surfactants*, Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono- and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, e.g., methyl esters.

Oftentimes, some of these materials, such as vegetable or seed oils and their esters, can be used interchangeably as an agricultural adjuvant, as a liquid carrier or as a surface active agent.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this disclosure is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

Also described herein are method of controlling undesirable vegetation which include contacting undesirable vegetation or the locus thereof with or applying the composition of Formula I as described herein to the soil or water to prevent the emergence or growth of the undesirable vegetation. The methods of controlling undesirable vegetation described herein can be used in, but are not limited to, wheat, rice, corn, and pasture grass.

The present compositions can be applied to weeds or their locus (i.e., area adjacent to the weed) by the use of conventional ground or aerial dusters, sprayers, and granule applicators, by addition to irrigation or flood water, and by other conventional means known to those skilled in the art.

In some embodiments, the compounds and compositions described herein are applied as a post-emergence application, pre-emergence application, in-water application to flooded paddy rice or water bodies (e.g., ponds, lakes and streams), or burn-down application.

In some embodiments, the compounds and compositions provided herein are utilized to control weeds in crops, including but not limited to citrus, apple, rubber, oiled palm, forestry, direct-seeded, water-seeded and transplanted rice, wheat, barley, oats, rye, sorghum, corn/maize, pastures, grasslands, rangelands, fallowland, turf, tree and vine orchards, aquatics, or row-crops, as well as non-crop settings, e.g., industrial vegetation management or rights of way. In some embodiments, the compounds and compositions are used to control woody plants, broadleaf and grass weeds, or sedges.

In some embodiments, the compounds and compositions provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (fall panicum, PANDI), *Paspalum dilatatum* Poir. (dallisgrass, PASDI), *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SPCJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (monochoria, MOOKA), *Monochoria vaginalis* (Burnt F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the compounds and compositions provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the compounds and compostions provided herein are utilized to control undesirable vegetation in range and pasture. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the compounds and compositions provided herein are utilized to control undesirable vegetation found in row crops. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly sida, SIDSP), *Sinapis*

*arvensis* L. (wild mustard, SINAR), *Solanum ptychanthum* Dunal (eastern black nightshade, SOLPT), or *Xanthium strumarium* L. (common cocklebur, XANST).

In some embodiments, application rates of about 1 to about 4,000 grams/hectare (g/ha) are employed in post-emergence operations. In some embodiments, rates of about 1 to about 4,000 g/ha are employed in pre-emergence operations. Application rates about 10 g/ha to about 1000 g/ha are preferred in post-emergent and pre-emergent operations. Application rates of about 20 g/ha to about 500 g/ha are most preferred in post-emergent pre-emergent operations.

In some embodiments, the compounds, compositions, and methods provided herein are used in conjunction with one or more other herbicides to control a wider variety of undesirable vegetation When used in conjunction with other herbicides, the presently claimed compounds can be formulated with the other herbicide or herbicides, tank-mixed with the other herbicide or herbicides or applied sequentially with the other herbicide or herbicides. Some of the herbicides that can be employed in conjunction with the compounds of the present disclosure include: 4-CPA; 4-CPB; 4-CPP; 2,4-D; 2,4-D choline salt, 2,4-D esters and amines; 2,4-DB; 3,4-DA; 3,4-DB; 2,4-DEB, 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+ isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-ammonium, glyphosate, halosafen, halosulfuron-methyl, haloxydine, haloxyfop-methyl, haloxyfop-P-methyl, halauxifen-methyl, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufenethyl, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-methyl, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, triallate, triasulfuron, triaziflam, tribenuron, tricamba, triclopyr esters and amines, tridiphane, trietazine, trifloxysulfuron, trifluralin, triflusulfuron, trifop, trifopsime, trihydroxytriazine, trimeturon, tripropindan, tritac, tritosulfuron, vernolate and xylachlor.

The compounds and compositions of the present disclosure can generally be employed in combination with known herbicide safeners, such as benoxacor, benthiocarb, brassinolide, cloquintocet (e.g., mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, MG 191, MON 4660, naphthalic anhydride (NA), oxabetrinil, R29148 and N-phenylsulfonylbenzoic acid amides, to enhance their selectivity.

The compounds, compositions, and methods described herein may be used to control undesirable vegetation in glyphosate tolerant, glufosinate tolerant, dicamba tolerant, phenoxy auxin tolerant, pyridyloxy auxin tolerant, aryloxyphenoxypropionate tolerant, acetyl CoA carboxylase (ACCase) inhibitor tolerant, imidazolinone tolerant, acetolactate synthase (ALS) inhibitortolerant, 4-hydroxyphenyl-pyruvate dioxygenase (HPPD) inhibitor tolerant, protoporphyrinogen oxidase (PPO) inhibitor tolerant, triazine tolerant, bromoxynil tolerant crops (such as, but not limited to, soybean, cotton, canola/oilseed rape, rice, cereals, corn, turf, etc), for example, in conjunction with glyphosate, glufosinate, dicamba, phenoxy auxins, pyridyloxy auxins, aryloxyphenoxypropionates, ACCase inhibitors, imidazolinones, ALS inhibitors, HPPD inhibitors, PPO inhibitors, triazines, and bromoxynil The compositions and methods may be used in controlling undesirable vegetation in crops possessing multiple or stacked traits conferring tolerance to multiple chemistries and/or inhibitors of multiple modes of action.

The compounds and compositions provided herein may also be employed to control herbicide resistant or tolerant weeds. Exemplary resistant or tolerant weeds include, but are not limited to, biotypes resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes-of-action.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

General Considerations: Fluorine spectra were acquired at 376 MHz on a Bruker DRX400 spectrometer. The spectra were referenced to trichlorofluoromethane ($CFCl_3$) as an external standard and were typically conducted with proton decoupling.

Example 1

Preparation of methyl 4-amino-3-chloro-6-vinylpicolinate (C1)

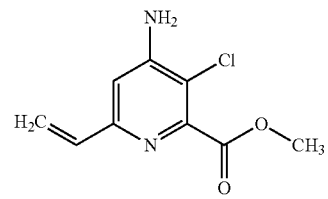

A mixture of methyl 4-amino-3,6-dichloropicolinate (2.50 g, 11.3 mmol), vinyl tributyltin (7.17 g, 22.6 mmol), and bis(triphenylphosphine)palladium(II) chloride (1.19 g, 1.70 mmol) in 1,2-dichloroethane (12 mL) was capped in a 25-mL vial and heated at 120° C. for 30 minutes in a Biotage Initiator® microwave reactor with external IR-sensor temperature monitoring from the side of the vessel. The mixture was loaded directly onto a silica gel cartridge and purified by flash column chromatography (0-40% ethyl acetate/hexanes) to afford the title compound as a yellow solid (2.03 g, 84%): mp 74.5-76.5° C.; $^1$H NMR (400 MHz, $CDCl_3$) δ 6.78 (s, 1H), 6.68 (dd, J=17.5, 10.8 Hz, 1H), 6.10 (d, J=17.5 Hz, 1H), 5.48 (d, J=10.8 Hz, 1H), 4.75 (s, 2H), 3.98 (s, 3H); $^{13}$C NMR (400 MHz, $CDCl_3$) δ 165.8, 154.0, 150.3, 148.0, 135.8, 119.3, 113.5, 107.7, 52.9; ESIMS m/z 213 ([M+H]$^+$). The following compounds were prepared in accordance to the procedure in Example 1:

Methyl 4-amino-3,5-dichloro-6-vinylpicolinate (C2)

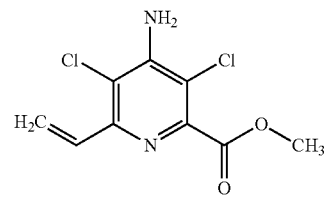

Isolated as a yellow solid (1.73 g, 60%): mp 103-105° C.; $^1$H NMR (400 MHz, $CDCl_3$) δ 7.12 (dd, J=16.9, 10.7 Hz, 1H), 6.49 (dd, J=16.9, 1.8 Hz, 1H), 5.62 (dd, J=10.7, 1.8 Hz, 1H), 5.20 (s, 2H), 3.98 (s, 3H); $^{13}$C NMR (101 MHz, $CDCl_3$) δ 165.28, 149.36, 147.24, 145.27, 130.66, 122.81, 115.68, 112.95, 52.91; ESIMS m/z 246 ([M+H]$^-$).

Methyl 6-allyl-4-amino-3-chloropicolinate (C3)

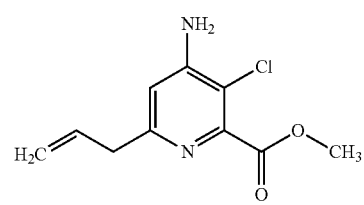

Isolated as an impure solid (4.10 g) used without further purification in the next step: ESIMS m/z 227 ([M+H]+).

Methyl 4-acetamido-3-chloro-6-vinylpicolinate (C4)

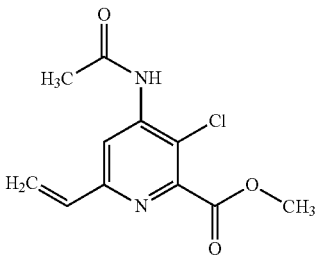 [SMILES: C=Cc1cc(NC(C)=O)c(Cl)c(C(=O)OC)n1]

Isolated as a white solid (0.611 g, 63%): mp 107-108° C.; $^1$H NMR (400 MHz, CDCl$_3$) δ 8.64 (s, 1H), 7.92 (s, 1H), 6.79 (dd, J=17.5, 10.8 Hz, 1H), 6.25 (dd, J=17.4, 0.9 Hz, 1H), 5.57 (dd, J=10.8, 0.9 Hz, 1H), 4.00 (s, 3H), 2.31 (s, 3H); EIMS m/z 254 ([M+H]+).

Methyl 6-allyl-4-amino-3-chloro-5-fluoropicolinate (C5)

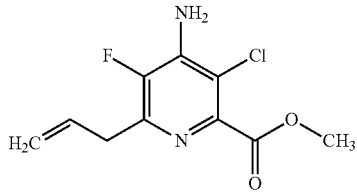 [SMILES: C=CCc1nc(C(=O)OC)c(Cl)c(N)c1F]

Isolated as a yellow oil (2.30 g, 66%): $^1$H NMR (400 MHz, CDCl$_3$) δ 6.09-5.91 (m, 1H), 5.22-5.05 (m, 2H), 4.78 (s, 2H), 3.97 (s, 3H), 3.57 (ddt, J=6.5, 2.9, 1.5 Hz, 2H); $^{19}$F NMR (400 MHz, CDCl$_3$) δ -142.3; ESIMS m/z 245 ([M+H]+).

Example 2

Preparation of methyl 4-amino-3-chloro-6-(1-fluorovinyl)picolinate (F6)

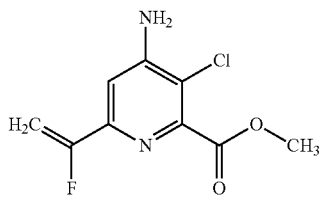

A mixture of methyl 4-acetamido-3,6-dichloropicolinate (0.528 g, 2.01 mmol), tributyl(1-fluorovinyl)stannane (1.00 g, 3.00 mmol), and bis(triphenylphosphine)palladium(II) chloride (0.225 g, 0.320 mmol) in 1,2-dichloroethane (4 mL) was heated at 80° C. for 8 hours. The reaction mixture was directly purified by flash column chromatography (0-50% ethyl acetate/hexanes) to afford methyl 4-acetamido-3-chloro-6-(1-fluorovinyl)picolinate (0.512 g) as an impure mixture. To the crude intermediate in methanol (19 mL) at 0° C. was added acetyl chloride (2.90 mL, 37.6 mmol) dropwise. The ice bath was removed after 30 minutes, and the reaction mixture was warmed to room temperature stirring overnight. The methanol was removed by vacuum, and the reaction mixture was neutralized with saturated aqueous sodium bicarbonate. This aqueous solution was extracted three times with ethyl acetate, dried over anhydrous sodium sulfate, filtered, and concentrated. The crude product was purified by reverse-phase flash column chromatography (0-40, 40-40, 40-100% acetonitrile/water). A crude $^1$H NMR showed a mixture of deprotected products and purification by flash column chromatography (0-30, 30-30, 30-50% ethyl acetate/hexanes) afforded the title compound as a white powder (0.104 g, 24%).

Example 3

Preparation of methyl 4-amino-3-chloro-5-fluoro-6-(1-fluorovinyl)picolinate (F22)

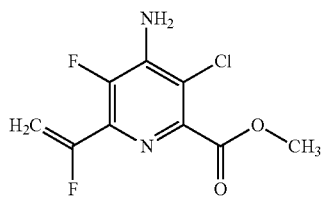 [SMILES: C=C(F)c1nc(C(=O)OC)c(Cl)c(N)c1F]

A mixture of methyl 4-amino-3,6-dichloro-5-fluoropicolinate (0.374 g, 1.57 mmol), tributyl(1-fluorovinyl)stannane (0.590 g, 1.76 mmol), and bis(triphenylphosphine)palladium (II) chloride (0.175 g, 0.250 mmol) in 1,2-dichloroethane (7 mL) was heated at 70° C. for 3 hours. The reaction mixture was directly purified by flash column chromatography (0-60% ethyl acetate/hexanes). A second purification by reverse-phase flash column chromatography (0-40, 40-40, 40-100% acetonitrile/water) afforded the title compound as a white powder (0.0810 g, 21%).

Example 4

Preparation of methyl 4-amino-3,5-dichloro-6-(3,3,3-trifluoropropyl)picolinate (F17)

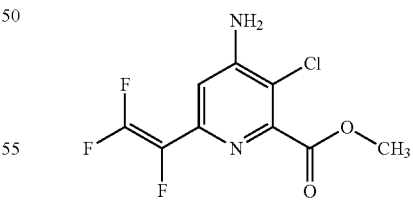

A mixture of tributyl(1,2,2-trifluorovinyl)stannane (Raghavanpillai, A.; Burton, D. J. *Journal of Organic Chemistry* 2004, 69(21), 7083-7091) (1.50 g, 4.04 mmol), methyl 4-amino-3-chloro-6-iodopicolinate (0.842 g, 2.69 mmol) and bis(triphenylphosphine)palladium (II) dichloride (0.284 g, 0.404 mmol) in 1,2-dichloroethane (6.74 mL) was capped in a 25-mL vial and heated at 120° C. for 30 minutes in a Biotage Initiator® microwave reactor with external IR-sensor temperature monitoring from the side of the vessel.

The reaction mixture was adsorbed onto Celite® and purified by flash column chromatography (ethyl acetate/hexanes gradient) to afford the title compound as a yellow solid (0.243 g, 34%).

Example 5

Preparation of Methyl 4-amino-3-chloro-6-(1-ethoxyvinyl)-5-fluoropicolinate (C6)

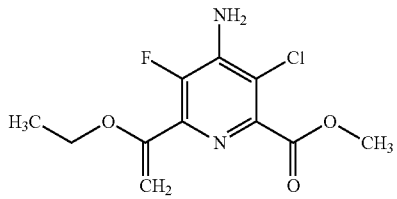 [SMILES: C=C(OCC)c1nc(C(=O)OC)c(Cl)c(N)c1F]

A mixture of methyl 4-amino-3,6-dichloro-5-fluoropicolinate (1.65 g, 6.90 mmol), tributyl(1-ethoxyvinyl)stannane (4.99 g, 13.8 mmol), and bis(triphenylphosphine)palladium (II) chloride (0.485 g, 0.690 mmol) in 1,2-dichloroethane (13.8 mL) was capped in a 25-mL vial and heated at 120° C. for 30 minutes in a Biotage Initiator® microwave reactor with external IR-sensor temperature monitoring from the side of the vessel. The cooled reaction mixture was applied directly to a silica gel column and purified by flash column chromatography (0-100% ethyl acetate/methylene chloride and reverse-phase flash column chromatography (0-100% acetonitrile/water) to provide the title compound as a pale yellow solid (1.30 g, 69%): $^1$H NMR (400 MHz, CDCl$_3$) δ 4.88 (s, 2H), 4.85 (dd, J=2.6, 0.9 Hz, 1H), 4.53 (d, J=2.7 Hz, 1H), 3.96 (s, 3H), 3.94 (q, J=7.3 Hz, 2H), 1.40 (t, J=7.0 Hz, 3H); $^{19}$F NMR (376 MHz, CDCl$_3$) δ −138.00; ESIMS m/z 275 ([M+H]$^+$).

The following compounds were prepared in accordance to the procedure in Example 5:

Methyl 4-amino-3,5-dichloro-6-(1-ethoxyvinyl)picolinate (C7)

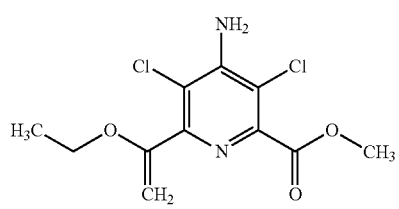 [SMILES: C=C(OCC)c1nc(C(=O)OC)c(Cl)c(N)c1Cl]

Isolated as a yellow solid: $^1$H NMR (400 MHz, CDCl$_3$) δ 5.28 (s, 2H), 4.51 (dd, J=15.2, 2.7 Hz, 2H), 3.95 (s, 3H), 3.94 (q, J=14.1, 7.0 Hz, 2H), 1.38 (t, J=7.0 Hz, 3H); ESIMS m/z 289 ([M−H]$^−$).

Methyl 4-amino-3-chloro-6-(1-ethoxyvinyl)picolinate (C8)

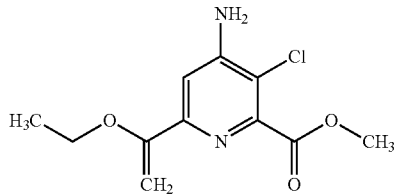 [SMILES: C=C(OCC)c1cc(N)c(Cl)c(C(=O)OC)n1]

Isolated as a sticky oil: $^1$H NMR (400 MHz, CDCl$_3$) δ 7.12 (s, 1H), 5.43 (d, J=2.0 Hz, 1H), 4.76 (s, 2H), 4.36 (d, J=2.0 Hz, 1H), 3.97 (s, 3H), 3.93 (q, J=7.0 Hz, 2H), 1.41 (t, J=7.0 Hz, 3H); ESIMS m/z 257 ([M+H]$^+$).

Example 6

Preparation of methyl 4-amino-3-chloro-5-fluoro-6-vinylpicolinate (C9)

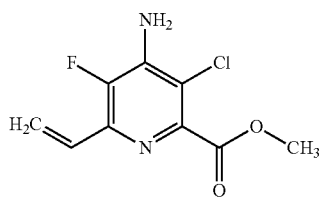

A mixture of methyl 4-amino-3,6-dichloro-5-fluoropicolinate (3.00 g, 12.6 mmol), vinyl tributyltin (8.32 g, 26.2 mmol), and bis(triphenylphosphine)palladium(II) chloride (1.32 g, 1.88 mmol) in 1,2-dichloroethane (24 mL) was capped in a 25-mL vial and heated at 120° C. for 30 minutes in a Biotage Initiator® microwave reactor with external IR-sensor temperature monitoring from the side of the vessel. The mixtures were loaded directly onto a silica gel cartridge and purified by flash column chromatography (0-40% ethyl acetate/hexanes) to provide the title compound as a yellow solid (2.48 g, 86%): mp 70-72° C.; $^1$H NMR (400 MHz, CDCl$_3$) δ 6.89 (ddd, J=17.4, 11.0, 1.5 Hz, 1H), 6.40 (dd, J=17.4, 1.6 Hz, 1H), 5.63 (dd, J=11.0, 1.5 Hz, 1H), 4.81 (s, 2H), 3.98 (s, 3H); $^{19}$F NMR (400 MHz, CDCl$_3$) δ −144.1; ESIMS m/z 229 ([M−H]$^−$).

Example 7

Preparation of methyl 4-amino-3-chloro-6-(prop-1-en-2-yl)picolinate (C10)

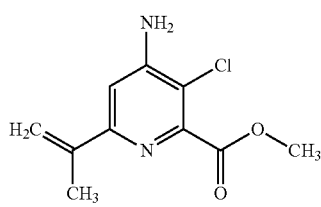

A mixture of picolinate methyl 4-amino-3,6-dichloropicolinate (0.929 g, 4.20 mmol), isopropenylboronic acid pinacol ester (1.06 g, 6.31 mmol), bis(triphenylphosphine)palladium(II) chloride (0.392 g, 0.560 mmol), and potassium fluoride (0.809 g, 13.9 mmol) in acetonitrile/water (12 mL, 3:1) was heated at 85° C. for 17 hours. Additional isopropenylboronic acid pinacol ester (0.500 mL, 2.66 mmol) was added and the reaction was heated at 85° C. for 24 hours. Additional isopropenylboronic acid pinacol ester (0.300 mL, 1.60 mmol) was added and the reaction was heated at 85° C. for 24 hours. The reaction was cooled, diluted with brine, and extracted twice with ethyl acetate. The organic layers were dried over magnesium sulfate, filtered, and adsorbed onto silica gel. Purification by flash column chromatography (0-20, 20-20, 20-60% ethyl acetate/hexanes) afforded the title compound as a pink oil (0.234 g, 25%): $^1$H NMR (400 MHz, CDCl$_3$) δ 6.83 (s, 1H), 5.83 (dd, J=1.7, 0.8 Hz, 1H), 5.32-5.19 (m, 1H), 4.75 (s, 2H), 3.97 (s, 3H), 2.13 (dd, J=1.5, 0.8 Hz, 3H); $^{13}$C NMR (101 MHz, CDCl$_3$) δ 166.03, 156.46, 150.15, 147.69, 141.85, 116.71, 113.05, 106.97, 52.78, 20.40; EIMS m/z 226 ([M]$^+$).

The following compounds were prepared in accordance to the procedure in Example 7:

Methyl 4-amino-3-chloro-5-fluoro-6-(prop-1-en-2-yl)picolinate (C11)

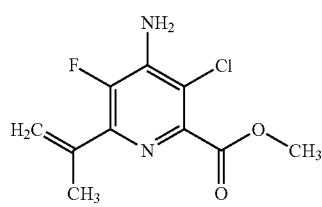 [SMILES: C=C(C)c1nc(C(=O)OC)c(Cl)c(N)c1F]

Isolated as a white solid (0.57 g, 59%): mp 98-100° C.; $^1$H NMR (400 MHz, CDCl$_3$) δ 5.73-5.61 (m, 1H), 5.49 (d, J=1.6 Hz, 1H), 4.79 (s, 2H), 3.97 (s, 3H), 2.18 (d, J=0.9 Hz, 3H); $^{19}$F NMR (376 MHz, CDCl$_3$) δ -138.80; ESIMS m/z 243 ([M-H]$^-$).

Example 8

Preparation of methyl 4-amino-3-chloro-6-formylpicolinate (C12)

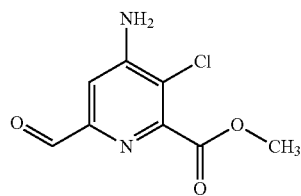

A solution of methyl 4-amino-3-chloro-6-vinylpicolinate (2.03 g, 9.55 mmol) in methylene chloride (140 mL) in a three-neck round bottom flask was cooled to −78° C. Ozone was bubbled through the solution for 30 minutes. The reaction mixture was purged with oxygen for 20 minutes. Triphenylphosphine (2.77 g, 10.6 mmol) was added, and the reaction was stirred at room temperature for 18 hours. The reaction was adsorbed onto silica gel and purified by flash column chromatography (0-20% ethyl acetate/methylene chloride) to afford the title compound as a yellow oil (0.610 g, 30%): $^1$H NMR (400 MHz, CDCl$_3$) δ 9.95 (s, 1H), 7.35 (s, 1H), 5.03 (s, 2H), 4.04 (s, 3H); IR (KBr thin film) 3472, 3366, 3207, 1710, 1626 cm$^{-1}$; ESIMS m/z 213 ([M-H]$^-$).

The following compounds were prepared in accordance to the procedure in Example 8:

Methyl 4-amino-3,5-dichloro-6-formylpicolinate (C13)

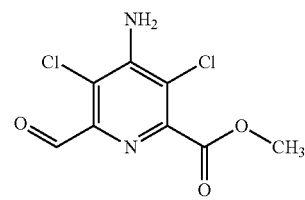

Isolated as a yellow solid (1.30 g, 75%): mp 171-174° C.; $^1$H NMR (400 MHz, CDCl$_3$) δ 10.11 (s, 1H), 5.51 (s, 2H), 4.02 (s, 3H); $^{13}$C NMR (101 MHz, CDCl$_3$) δ 189.79, 164.28, 148.77, 145.77, 144.56, 132.16, 117.43, 53.28; ESIMS m/z 248 ([M-H]$^-$).

Example 9

Preparation of methyl 4-(di-tert-butyloxycarbonyl)amino-3-chloro-6-vinylpicolinate (C14)

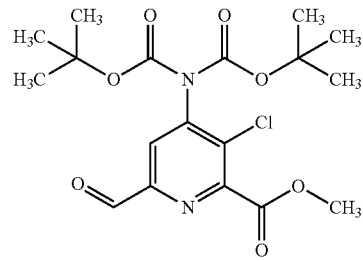 [SMILES: COC(=O)c1nc(C=O)cc(N(C(=O)OC(C)(C)C)C(=O)OC(C)(C)C)c1Cl]

A solution of methyl 4-(di-tert-butyloxycarbonyl)amino-3-chloro-6-vinylpicolinate (3.30 g, 7.99 mmol) in methylene chloride (80 mL) was cooled to −78° C. and ozone was bubbled through the solution until it turned blue. Oxygen was bubbled through the solution until it returned to a clear color. Triphenylphosphine (2.52 g, 9.59 mmol) was added, and the reaction was stirred at room temperature overnight. The reaction mixture was directly purified by flash column chromatography (0-100% ethyl acetate/hexanes) to afford the title compound as a light yellow solid (2.23 g, 67%): mp 109-110° C.; $^1$H NMR (400 MHz, CDCl$_3$) δ 10.07 (s, 1H), 7.91 (s, 1H), 4.07 (s, 3H), 1.42 (s, 18H).

Example 10

Preparation of methyl 4-amino-3-chloro-5-fluoro-6-formylpicolinate (C15)

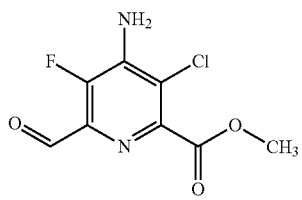

A solution of methyl 4-amino-3-chloro-5-fluoro-6-vinylpicolinate (1.77 g, 7.67 mmol) in methylene chloride (215 mL) in a three-neck round bottom flask was cooled to −78° C. Ozone was bubbled through the solution for 45 minutes in which the reaction coor turned from pale yellow to blue. The reaction mixture was purged with oxygen for 30 minutes. Triphenylphosphine (2.42 g, 9.21 mmol) was added, and the reaction was stirred at room temperature for 18 hours. The reaction was adsorbed onto silica gel and purified by flash column chromatography (0-30% ethyl acetate/methylene chloride) to provide the title compound as a yellow oil (1.27 g, 71%): $^1$H NMR (400 MHz, CDCl$_3$) δ 10.07 (d, J=1.1 Hz, 1H), 5.09 (s, 2H), 4.02 (s, 3H); $^{19}$F NMR (400 MHz, CDCl$_3$) δ −141.9; IR (KBr neat film) 3464, 3313, 3179, 2963, 2919, 1735, 1702, 1610, 1492, 1245, 1203 cm$^{-1}$; ESIMS m/z 231 ([M−H]$^-$).

Example 11

Preparation of methyl 4-(di-tert-butyloxycarbonyl)amino-3-chloro-6-(2-hydroxyethyl)picolinate (C16)

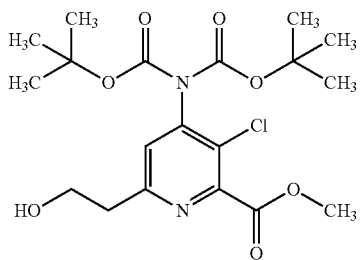 [SMILES: COC(=O)c1nc(CCO)cc(N(C(=O)OC(C)(C)C)C(=O)OC(C)(C)C)c1Cl]

A solution of methyl 6-allyl-4-(di-tert-butyloxycarbonyl)amino-3-chloropicolinate (1.01 g, 2.37 mmol) in methylene chloride (45 mL) and methanol (2 mL) was cooled to −78° C., and ozone was bubbled through the solution for 15 minutes. Oxygen was bubbled through the solution for 15 minutes and the reaction was diluted with methanol (15 mL). Sodium acetate (0.233 g, 2.84 mmol) and sodium borohydride (0.134 g, 3.55 mmol) in water were then added. The reaction mixture was warmed to room temperature and stirred over the weekend. The reaction was diluted with water (75 mL) and extracted twice with ethyl acetate (250 mL). The organic layers were dried over anhydrous sodium sulfate, filtered, and concentrated to afford yellow oil (761 mg) that appeared to be a mixture of the title compound and the monoboc derivative. This crude product was carried on in the next step without further purification.

The following compounds were prepared in accordance to the procedure in Example 11:

Methyl 4-(di-tert-butyloxycarbonyl)amino-3-chloro-5-fluoro-6-(2-hydroxyethyl)-picolinate (C17)

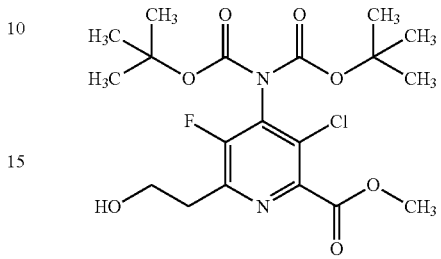

Isolated as a yellow oil (1.327 g, 85%): $^1$H NMR (400 MHz, CDCl$_3$) δ 4.08 (t, J=5.6 Hz, 2H), 3.99 (s, 3H), 3.12 (td, J=5.6, 2.1 Hz, 2H), 1.43 (s, 18H); $^{19}$F NMR (376 MHz, CDCl$_3$) δ −124.73; ESIMS m/z 449 ([M+H]$^+$).

Example 12

Preparation of methyl 4-amino-3-chloro-6-(1,2-dihydroxyethyl)picolinate (C18)

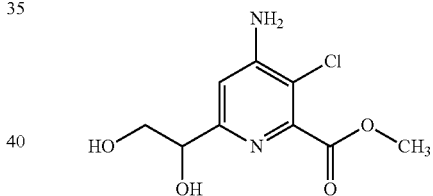

To methyl 4-amino-3-chloro-6-vinylpicolinate (1.18 g, 5.53 mmol) in water/tert-butanol (1:1, 5.5 mL) at room temperature was added N-methylmorpholine-N-oxide (0.777 g, 6.63 mmol), followed by a catalytic amount of 2.5 wt % osmium tetroxide in tert-butanol. The dark brown reaction mixture was stirred at room temperature for 3 hours. The methanol and tert-butanol were concentrated off under vacuum. The crude residue was diluted with ethyl acetate and quenched with sodium bisulfite (0.730 g, 7.00 mmol) in water (15 mL). The product was determined by thin layer chromatography to be present in aqueous layer. The aqueous layer was loaded onto a Celite® cartridge. The organic layer were dried over sodium sulfate, filtered, concentrated, and loaded onto a separate Celite® cartridge. Purification of both loaded cartridges by reverse-phase flash column chromatography (0-50% acetonitrile/water) afforded the title compound as a yellow oil (0.910 g, 67%): $^1$H NMR (400 MHz, CDCl$_3$) δ 6.83 (s, 1H), 5.46 (q, J=7.1 Hz, 1H), 3.80 (s, 3H), 1.75 (d, J=7.1 Hz, 3H); $^{13}$C NMR (101 MHz, CDCl$_3$) δ 165.38, 157.68, 150.75, 114.10, 107.56, 72.65, 66.75, 55.02, 52.91; ESIMS m/z 247 ([M+H]$^+$).

The following compounds were prepared in accordance to the procedure in Example 12:

Methyl 4-amino-3-chloro-6-(1,2-dihydroxypropan-2-yl)picolinate (C19)

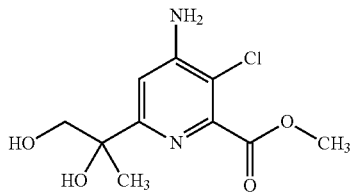 [SMILES: COC(=O)c1nc(C(C)(O)CO)cc(N)c1Cl]

Isolated as a brown solid (0.620 g, 71%): mp 179-182° C.; $^1$H NMR (400 MHz, DMSO-d$_6$) δ 7.08 (s, 1H), 6.59 (s, 2H), 4.99 (s, 1H), 4.59 (t, J=6.0 Hz, 1H), 3.85 (s, 3H), 3.45 (d, J=6.0 Hz, 2H), 1.29 (s, 3H); $^{13}$C NMR (101 MHz, DMSO-d$_6$) δ 166.02, 163.60, 151.32, 147.38, 109.47, 106.99, 74.69, 69.27, 52.38, 24.93; ESIMS m/z 261 ([M+H]$^+$).

Example 13

Preparation of methyl 4-(di-tert-butyloxycarbonyl)amino-3-chloro-6-(2-hydroxypropan-2-yl)picolinate (C20)

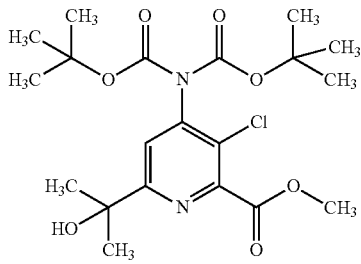 [SMILES: COC(=O)c1nc(C(C)(C)O)cc(N(C(=O)OC(C)(C)C)C(=O)OC(C)(C)C)c1Cl]

To a solution of methyl 4-(di-tert-butyloxycarbonyl)amino-3-chloro-6-(prop-1-en-2-yl)picolinate (WO 2010/011375) (510 mg, 1.20 mmol) in 1,2-dimethoxyethane/methanol (12 mL, 1:1) was added cobalt(II) mesotetraphenylporphine (0.0200 g, 0.0300 mmol) and stirred at room temperature overnight. Tetraethylammoniumborohydride (0.260 g, 1.80 mmol) was added and stirred at room temperature for 5 hours. The reaction mixture was quenched with saturated aqueous sodium bicarbonate (10 mL) and extracted twice with ethyl acetate. The organic layers were dried over sodium sulfate, filtered, and concentrated. The crude product was purified by reverse-phase flash column chromatography (0-70, 75-75, 75-100% acetonitrile/water) to afford the title compound as a pink brittle solid (0.171 g, 32%): $^1$H NMR (400 MHz, CDCl$_3$) δ 7.43 (s, 1H), 4.01 (s, 3H), 3.98 (s, 1H), 1.57 (s, 6H), 1.41 (s, 18H); $^{13}$C NMR (101 MHz, CDCl$_3$) δ 165.50, 164.68, 149.24, 147.46, 147.06, 127.25, 121.81, 84.20, 72.27, 53.01, 30.40, 27.77; ESIMS m/z 446 ([M+H]$^+$).

The following compounds were prepared in accordance to the procedure in Example 13:

Methyl 4-(di-tert-butyloxycarbonyl)amino-3-chloro-5-fluoro-6-(2-hydroxypropan-2-yl)picolinate (C21)

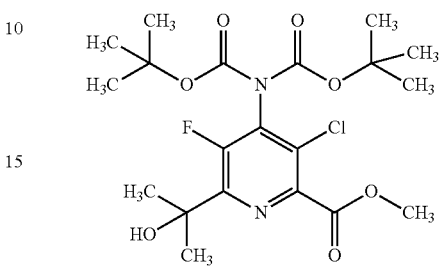

Isolated as a clear oil (0.053 g, 28%): $^1$H NMR (400 MHz, CDCl$_3$) δ 4.93 (s, 1H), 4.01 (s, 3H), 1.61 (d, J=1.6 Hz, 6H), 1.42 (s, 18H); $^{19}$F NMR (376 MHz, CDCl$_3$) δ −121.23; ESIMS m/z 463 ([M+H]$^-$).

Example 14

Preparation of methyl 4-(di-tert-butyloxycarbonyl)amino-3-chloro-6-(1-hydroxypropan-2-yl)picolinate (C22)

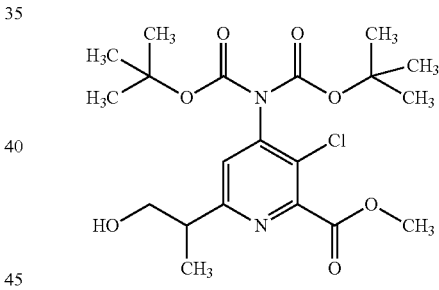

To a solution of methyl 4-(di-tert-butyloxycarbonyl)amino-3-chloro-6-(prop-1-en-2-yl)picolinate (0.530 g, 1.24 mmol) in tetrahydrofuran (2.5 mL) at 0° C. was added borane-methyl sulfide complex (0.130 mL, 1.37 mmol) dropwise. The reaction mixture was stirred at room temperature for 2 hours. An aqueous saturated sodium bicarbonate solution (2 mL) and a 30% hydrogen peroxide solution (1 mL) were added and stirred vigorously for 1 hour. The mixture was poured into saturated sodium bicarbonate and extracted three times with ethyl acetate. The combined organic layer was dried over anhydrous sodium sulfate, filtered, and concentrated to afford the title compound as a clear oil (0.368 g, 67%): $^1$H NMR (400 MHz, CDCl$_3$) δ 7.22 (s, 1H), 3.99 (s, 3H), 3.96-3.81 (m, 2H), 3.26 (t, J=6.3 Hz, 1H), 3.14 (pd, J=7.0, 4.0 Hz, 1H), 1.41 (s, 18H), 1.33 (d, J=7.2 Hz, 3H); $^{13}$C NMR (101 MHz, CDCl$_3$) δ 164.68, 163.88, 149.50, 147.92, 147.04, 127.48, 125.37, 84.35, 66.65, 53.20, 42.05, 27.91, 17.07.

Example 15

Preparation of methyl 4-amino-3-chloro-6-(difluoromethyl)picolinate (F12)

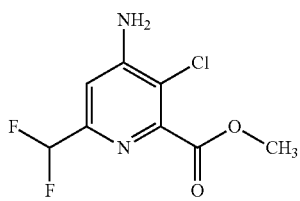

A solution of methyl 4-amino-3-chloro-6-formylpicolinate (0.597 g, 2.78 mmol) in chloroform (19 mL) was cooled in an ice bath. Deoxo-Fluor® (1.10 mL, 6.13 mmol) was added, and the reaction continued stirring in the ice bath for 10 minutes before removing and allowing the solution to warm to room temperature overnight. The reaction was quenched with methanol (13 mL), stirred at room temperature for 3.5 hours, and concentrated. The crude product was purified by flash column chromatography (0-5% ethyl acetate/methylene chloride) to afford the title compound as white solid (0.150 g, 23%).

The following compounds were prepared in accordance to the procedure in Example 15:

Methyl 4-amino-3,5-dichloro-6-(difluoromethyl)picolinate (F7)

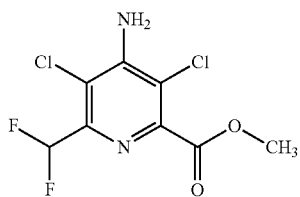 [SMILES: COC(=O)c1nc(C(F)F)c(Cl)c(N)c1Cl]

Isolated as a white solid (170 mg, 52%).

Example 16

Preparation of methyl 4-amino-3-chloro-6-(fluoromethyl)picolinate (F26)

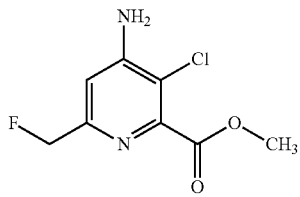

To a solution of methyl 4-amino-3-chloro-6-(hydroxymethyl)picolinate (0.129 g, 0.600 mmol) in methylene chloride (3 mL) at 0° C. was added Deoxo-Fluor® (0.140 mL, 0.760 mmol). The insoluble starting material had become soluble within 30 minutes. The reaction was allowed to warm to room temperature over 2.5 hours. The reaction was quenched with methanol, adsorbed onto silica gel, and purified by flash column chromatography (0-100% ethyl acetate/methylene chloride) to afford the title compound as a clear oil (0.0200 g, 15%).

The following compounds were prepared in accordance to the procedure in Example 16:

Methyl 4-amino-3-chloro-5-fluoro-6-(fluoromethyl)picolinate (F14)

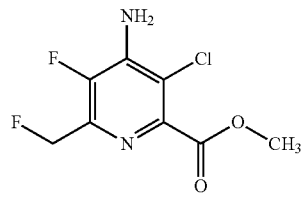

Isolated as clear oil (0.140 g, 44%).

Methyl 4-amino-3,5-dichloro-6-(fluoromethyl)picolinate (F1)

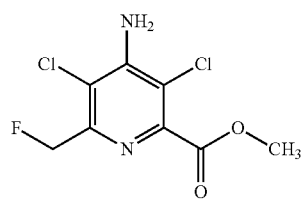

Isolated as a white solid (0.140 g, 66%).

Example 17

Preparation of methyl 4-amino-3-chloro-6-(2-fluoroethyl)picolinate (F31)

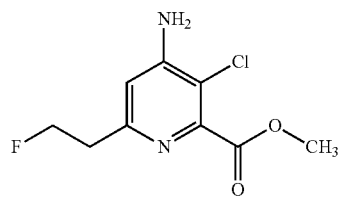

To a solution of methyl 4-(di-tert-butyloxycarbonyl) amino-3-chloro-6-(2-hydroxyethyl)picolinate (0.550 g, 1.28 mmol) in chloroform (11 mL) was added Deoxo-Fluor® (0.450 mL, 2.44 mmol) and stirred at room temperature overnight. The reaction was quenched with a few drops of saturated aqueous sodium bicarbonate and extracted with methylene chloride. The organic layer was dried over anhydrous sodium sulfate and filtered. Trifluoroacetic acid (3.00 mL, 39.1 mmol) was added, and the reaction was stirred at room temperature overnight. The reaction was neutralized with saturated aqueous sodium bicarbonate and stirred for 30 minutes, then extracted three times with methylene chloride, dried over anhydrous sodium sulfate, filtered, and concentrated. The crude product was purified by flash column chromatography (0-100% ethyl acetate/hexanes) to afford the title compound as a clear oil (0.0230 g, 8%).
The following compounds were prepared in accordance to the procedure in Example 17:

Methyl 4-amino-3-chloro-5-fluoro-6-(2-fluoroethyl)picolinate (F29)

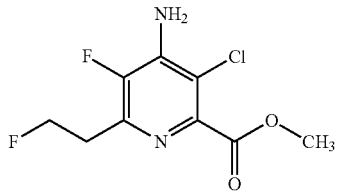 [SMILES: COC(=O)c1nc(CCF)c(F)c(N)c1Cl]

Isolated as a yellow oil (0.101 g, 44%).

Example 18

Preparation of methyl 4-amino-3-chloro-6-(1,2-difluoroethyl)picolinate (F28)

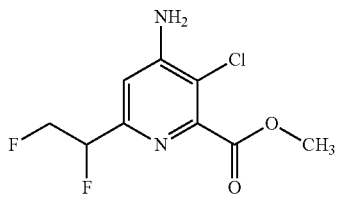 [SMILES: COC(=O)c1nc(C(F)CF)cc(N)c1Cl]

To methyl 4-amino-3-chloro-6-(1,2-dihydroxyethyl)picolinate (0.54 g, 2.2 mmol) was added chloroform (7.3 mL), in which the starting material as an oil remained insoluble. The solution was stirred in an ice bath and Deoxo-Fluor® (1.5 mL, 8.2 mmol) was added dropwise. The reaction was stirred at room temperature overnight, then loaded directly onto a Celite® cartridge and dried in vacuum oven. Purification by reverse-phase flash column chromatography (0-50, 50-50, 50-100% acetonitrile/water) provided a brown oil (0.16 g). This crude residue was loaded onto a silica gel cartridge and dried in vacuum oven. Purification by flash column chromatography (0-50% ethyl acetate/hexanes) provided the title compound as a clear oil (0.069 g, 13%).
The following compounds were prepared in accordance to the procedure in Example 18:

Methyl 4-amino-3-chloro-6-(1,2-difluoropropan-2-yl)picolinate (F11)

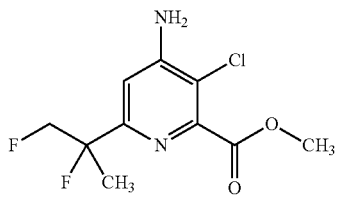 [SMILES: COC(=O)c1nc(C(C)(F)CF)cc(N)c1Cl]

Isolated as a white solid (0.0186 g, 7%).

Example 19

Preparation of methyl 4-amino-3-chloro-6-(2-fluoropropan-2-yl)picolinate (F9)

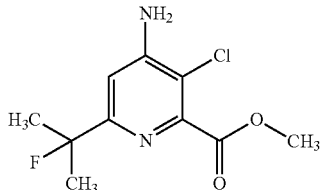

To a solution of methyl 4-(di-tert-butyloxycarbonyl)amino-3-chloro-6-(2-hydroxypropan-2-yl)picolinate (0.165 g, 0.370 mmol) in chloroform (1 mL) at 0° C. was added Deoxo-Fluor® (0.900 mL, 0.480 mmol) dropwise. The ice bath was removed after 10 minutes, and the reaction was warmed to room temperature over 1 hour. The reaction was quenched with saturated aqueous sodium bicarbonate (1 mL) and extracted with methylene chloride. The organic layer was dried over anhydrous sodium sulfate, filtered, and concentrated down to 1-2 mL of total volume. Trifluoroacetic acid (0.800 mL, 0.370 mmol) was added and stirred at room temperature overnight. The reaction was neutralized with saturated aqueous sodium bicarbonate and extracted twice with methylene chloride. The organic layers were dried over anhydrous sodium sulfate, filtered, and concentrated. The crude material was dissolved in methylene chloride and neutralized with saturated aqueous sodium bicarbonate until basic. The organic layer was dried over anhydrous sodium sulfate, filtered, and concentrated to afford the title compound as a tan solid (0.0340 g, 37% over two steps).
The following compounds were prepared in accordance to the procedure in Example 19:

Methyl 4-amino-3-chloro-5-fluoro-6-(2-fluoropropan-2-yl)picolinate (F8)

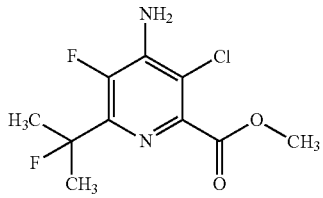 [SMILES: COC(=O)c1nc(C(C)(C)F)c(F)c(N)c1Cl]

Isolated as a yellow oil (0.022 g, 66%).

Example 20

Preparation of methyl 4-(di-tert-butyloxycarbonyl)amino-3-chloro-6-(1-fluoropropan-2-yl)picolinate (C23)

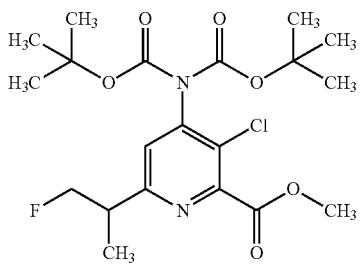 [SMILES: COC(=O)c1nc(C(C)CF)cc(N(C(=O)OC(C)(C)C)C(=O)OC(C)(C)C)c1Cl]

To a solution of methyl 4-(di-tert-butyloxycarbonyl)amino-3-chloro-6-(1-hydroxypropan-2-yl)picolinate (0.36 g, 0.81 mmol) in methylene chloride (3.2 mL) at 0° C. was added Deoxo-Fluor® (0.18 mL, 0.97 mmol). The reaction mixture was stirred at 0° C. for 2 hours and then purified directly by flash column chromatography (0-100% ethyl acetate/hexanes) to afford the title compound as a yellow oil (0.064 g, 18%): $^1$H NMR (400 MHz, CDCl$_3$) δ 7.22 (s, 1H), 4.62 (dddd, J=21.1, 14.3, 9.0, 6.0 Hz, 2H), 4.00 (s, 3H), 3.44-3.23 (m, 1H), 1.40 (s, 18H), 1.36 (dd, J=7.1, 1.1 Hz, 3H); ESIMS m/z 447 ([M]$^+$).

Example 21

Preparation of methyl 4-amino-3-chloro-5-fluoro-6-(1-fluoropropan-2-yl)picolinate (F37)

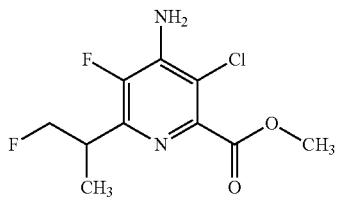 [SMILES: COC(=O)c1nc(C(C)CF)c(F)c(N)c1Cl]

To a solution of methyl 4-(di-tert-butyloxycarbonyl)amino-3-chloro-6-(1-hydroxypropan-2-yl)picolinate (0.30 g, 0.67 mmol) in methylene chloride (4 mL) at 0° C. was added Deoxo-Fluor® (0.19 mL, 1.0 mmol). After 2 hours, the reaction mixture was poured into saturated sodium bicarbonate and extracted three times with ethyl acetate. The combined organic layers were dried over sodium sulfate, filtered, and concentrated. The crude product was dissolved in methylene chloride (3 mL) and cooled to 0° C. Trifluoroacetic acid (3 mL) was added, and the reaction was stirred at room temperature overnight. The reaction mixture was poured into saturated sodium bicarbonate and extracted three times with ethyl acetate. The organic layers were dried over sodium sulfate, filtered, and concentrated. The residue was purified by flash column chromatography (0-100% ethyl acetate/hexanes) followed by reverse-phase HPLC (0-100% acetonitrile/water) to afford the title compound as a white solid (0.027 g, 15%).

Example 22

Preparation of methyl 4-amino-3-chloro-6-(2,2-difluoroethyl)-5-fluoropicolinate (F2)

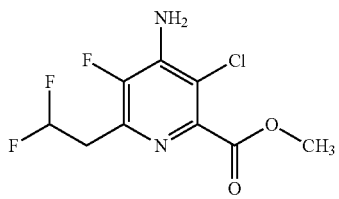 [SMILES: COC(=O)c1nc(CC(F)F)c(F)c(N)c1Cl]

To a solution of methyl 4-(di-tert-butyloxycarbonyl)amino-3-chloro-5-fluoro-6-(2-hydroxyethyl)picolinate (0.385 g, 0.860 mmol) in methylene chloride (5 mL) at 0° C. was added the Dess-Martin periodinane (0.437 g, 1.03 mmol) in one portion. After 15 minutes, Deoxo-Fluor® (1.90 g, 8.58 mmol) was added, and the reaction was stirred at 0° C. for an additional hour. The mixture was poured into saturated sodium bicarbonate and extracted three times with ethyl acetate. The organic layers were dried over anhydrous sodium sulfate, filtered, and concentrated. The residue was dissolved in methylene chloride (3.2 mL), cooled to 0° C., and trifluoroacetic acid (1 mL) was added. The reaction mixture was stirred at room temperature for 2 hours and then poured into saturated sodium bicarbonate and extracted three times with ethyl acetate. The organic layers were dried over anhydrous sodium sulfate, filtered, and purified by flash column chromatography (0-100% ethyl acetate/hexanes) to afford the title compound as a white solid (0.0460 g, 20%).

Example 23

Preparation of Methyl 4-amino-3-chloro-5-fluoro-6-(1-fluoroethyl)picolinate (F15)

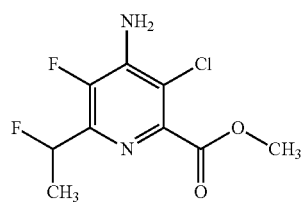 [SMILES: COC(=O)c1nc(C(C)F)c(F)c(N)c1Cl]

To a solution of methyl 4-amino-3-chloro-5-fluoro-6-(1-hydroxyethyl)picolinate (0.346 g, 1.39 mmol) in chloroform (9.3 mL) was added Deoxo-Fluor® (0.369 g, 1.67 mmol) dropwise maintaining the temperature below 30° C. The reaction mixture was stirred overnight at room temperature and then quenched with sodium bicarbonate (0.351 g, 4.17 mmol) in water (100 mL). The organic phase was dried, concentrated, and purified by flash column chromatography (100% hexanes) to provide the title compound as a white solid (0.260 g, 77%).

The following compounds were prepared in accordance to the procedure in Example 23:

Methyl 4-amino-3,5-dichloro-6-(1-fluoroethyl)picolinate (F10)

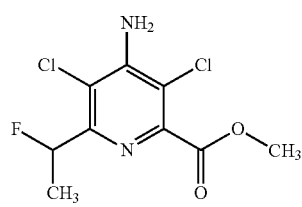 [SMILES: COC(=O)c1nc(C(C)F)c(Cl)c(N)c1Cl]

Methyl 4-amino-3-chloro-6-(1-fluoroethyl)picolinate (F19)

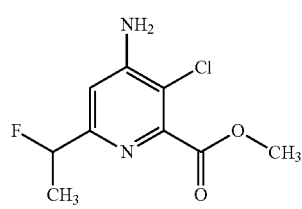

Example 24

Preparation of methyl 4-amino-3-chloro-6-(difluoromethyl)-5-fluoropicolinate (F3)

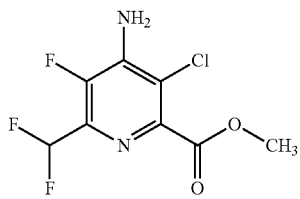

A solution of methyl 4-amino-3-chloro-5-fluoro-6-formylpicolinate (0.483 g, 2.08 mmol) in chloroform (13.8 mL) was cooled in an ice bath. Deoxo-Fluor® (0.840 mL, 4.57 mmol) was added, and the ice bath was removed and warmed to room temperature stirring overnight. The reaction was quenched with 10 mL of methanol and stirred at room temperature for 1 hour. The reaction mixture was concentrated and purified by flash column chromatography (5-40% ethyl acetate/hexanes) to provide the title compound as a white solid (0.371 g, 70%).

Example 25

Preparation of methyl 4-amino-3-chloro-6-(chloromethyl)picolinate (F35)

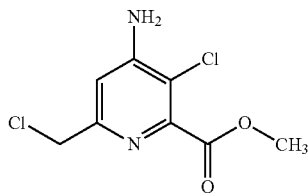

To a solution of methyl 4-amino-3-chloro-6-(hydroxymethyl)picolinate (0.103 g, 0.480 mmol) in 1,2-dichloroethane (1.2 mL) was added thionyl chloride (0.690 mL, 9.50 mmol). The reaction mixture was stirred at room temperature for 1.5 hours. The reaction was quenched with slow addition of methanol at 0° C. and adsorbed onto silica gel. Purification by flash column chromatography (0-100% ethyl acetate/hexanes/0.5% triethylamine) afforded the title compound as an off-white solid (0.0600 g, 54%).

The following compounds were prepared in accordance to the procedure in Example 25:

Methyl 4-amino-3-chloro-6-(chloromethyl)-5-fluoropicolinate (F21)

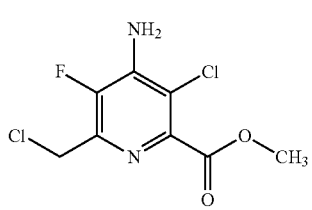

Isolated as a white solid (0.210 g, 77%).

Example 26

Preparation of methyl 4-amino-3,5-dichloro-6-(3,3,3-trifluoropropyl)picolinate (F5)

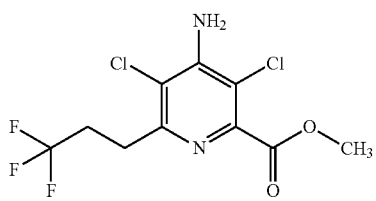 [SMILES: COC(=O)c1nc(CCC(F)(F)F)c(Cl)c(N)c1Cl]

To a solution of methyl 4-amino-6-(3,3,3-trifluoropropyl)picolinate (0.058 g, 0.23 mmol) in 1,2-dichloroethane (0.94 mL) was added N-chlorosuccinimide (0.094 g, 0.70 mmol) and heated at 60° C. overnight. The reaction had not gone to completion, so additional N-chlorosuccinimide (0.094 g, 0.70 mmol) was added and heated at 60° C. for 12 hours. The reaction was directly purified by flash column chromatography (0-100% ethyl acetate/hexanes) to afford the title compound as a yellow solid (0.036 g, 49%).

Example 27

Preparation of methyl 4-acetamido-6-(2-bromo-1-fluoroethyl)-3-chloropicolinate (C24) and methyl 4-acetamido-3-chloro-6-(1,2-dibromoethyl)picolinate (C25)

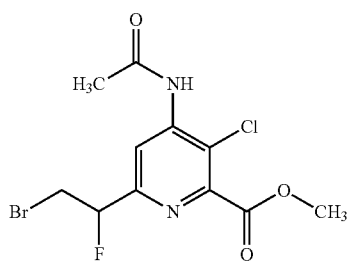

C24

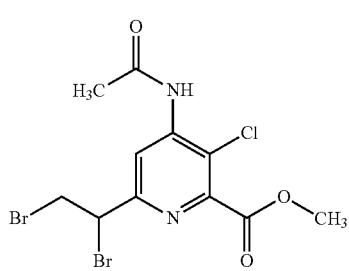

C25

To methyl 4-acetamido-3-chloro-6-vinylpicolinate (0.323 g, 1.27 mmol, 1 equiv) in methylene chloride (10 mL) was added N-bromosuccinimide (0.261 g, 1.50 mmol) at 0° C. Triethylamine.trihydrofluoride (0.620 mL, 3.80 mmol) was added dropwise, and the reaction was warmed to room temperature stirring overnight. The reaction mixture was quenched with water and solid sodium bicarbonate (0.533 g, 6.34 mmol) in small portions as gas evolution occurred. The biphasic mixture was separated and the aqueous layer was extracted with methylene chloride (2×). The combined organic layers were dried over sodium sulfate, filtered, and concentrated. The crude residue was loaded onto a Celite® cartridge and dried in vacuum oven overnight. Purification by reverse-phase flash column chromatography (0-40, 40-40, 40-100% acetonitrile/water) afforded the title compound C24 as a yellow oil (0.0715 g, 16%): $^1$H NMR (400 MHz, CDCl$_3$) δ 8.75 (s, 1H), 7.98 (s, 1H), 5.85-5.58 (m, 1H), 4.01 (s, 3H), 4.01-3.73 (m, 2H), 2.33 (s, 3H); $^{19}$F NMR (376 MHz, CDCl$_3$) δ −184.17; ESIMS m/z 354 ([M+H]$^+$) and title compound C25 as a yellow oil (0.0870 g, 17%): $^1$H NMR (400 MHz, CDCl$_3$) δ 8.69 (s, 1H), 7.97 (s, 1H), 5.18 (dd, J=11.0, 4.7 Hz, 1H), 4.33 (dd, J=11.0, 9.9 Hz, 1H), 4.01 (s, 3H), 4.00-3.95 (m, 1H), 2.32 (s, 3H); $^{13}$C NMR (101 MHz, CDCl$_3$) δ 168.86, 164.66, 156.19, 148.37, 143.15, 116.94, 114.68, 53.17, 48.52, 32.49, 25.22; ESIMS m/z 415 ([M+H]$^+$).

Example 28

Preparation of methyl 4-amino-3-chloro-6-(hydroxymethyl)picolinate (C26)

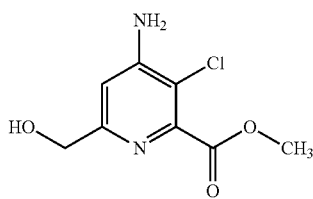

To a solution of methyl 4-amino-3-chloro-6-formylpicolinate (0.460 g, 2.14 mmol) in diethyl ether (20 mL) at 0° C. was added sodium borohydride (0.0810 g, 2.14 mmol). Due to the insolubility of methyl 4-amino-3-chloro-6-formylpicolinate, methanol (2 mL) was added. The reaction mixture was warmed to room temperature over 2 hours. A 2 N hydrochloric acid solution (1.1 mL, 2.14 mmol) was added and stirred for 30 minutes. The reaction mixture was diluted with ethyl acetate, washed with water, and extracted three times with ethyl acetate. The organic layers were dried over anhydrous magnesium sulfate, filtered, concentrated, and purified by flash column chromatography (0-100% ethyl acetate/hexanes) to afford the title compound as an oily white solid (0.237 g, 51%): $^1$H NMR (400 MHz, CDCl$_3$) δ 6.75 (s, 1H), 4.83 (s, 2H), 4.64 (d, J=4.2 Hz, 2H), 3.98 (s, 3H), 3.07 (d, J=4.6 Hz, 1H); ESIMS m/z 217 ([M+H]$^+$).
The following compounds were prepared in accordance to the procedure in Example 28:

Methyl 4-amino-3-chloro-5-fluoro-6-(hydroxymethyl)picolinate (C27)

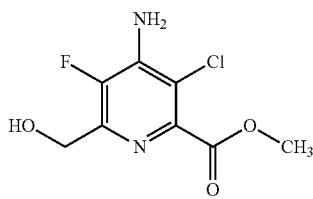

Isolated as a white solid (0.590 g, 65%): mp 129-131° C.; $^1$H NMR (400 MHz, CDCl$_3$) δ 4.87 (s, 2H), 4.76 (dd, J=5.4, 2.0 Hz, 2H), 3.98 (s, 3H), 3.39 (t, J=5.4 Hz, 1H); $^{19}$F NMR (400 MHz, CDCl$_3$) δ −145.9; ESIMS m/z 235 ([M+H]$^+$).

Methyl 4-amino-3,5-dichloro-6-(hydroxymethyl)picolinate (C28)

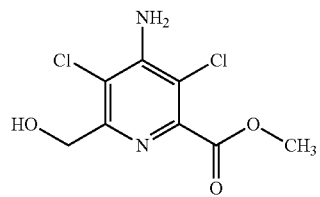

Isolated as a white solid (0.220 g, 44%): mp 108.0-109.3° C.; $^1$H NMR (400 MHz, CDCl$_3$) δ 5.26 (s, 2H), 4.71 (d, J=4.9 Hz, 2H), 3.98-3.96 (m, 4H); $^{13}$C NMR (101 MHz, CDCl$_3$) δ 164.76, 152.97, 147.22, 144.01, 114.39, 113.87, 61.39, 52.96; ESIMS m/z 250 ([M−H]$^-$).

Example 29

Preparation of Methyl 4-amino-3-chloro-5-fluoro-6-(1-hydroxyethyl)picolinate (C29)

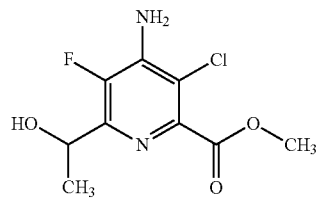

To a solution of methyl 6-acetyl-4-amino-3-chloro-5-fluoropicolinate (0.710 g, 2.88 mmol) in methanol (115 mL) was added sodium borohydride (0.109 g, 2.88 mmol) and stirred at room temperature for 2 hours. The reaction was quenched with 2 N hydrochloric acid (5 mL) and stirred for 1 hour before concentrating under vacuum and partitioning between ethyl acetate and water. The organic layer was concentrated, and the crude product was purified by flash column chromatography (amine column, 2-20% ethyl acetate/methylene chloride) to provide the title compound as a white solid (0.392 g, 55%): mp 122-124° C.; $^1$H NMR (400 MHz, CDCl$_3$) δ 5.04 (pd, J=6.6, 1.7 Hz, 1H), 4.87 (s, 2H), 4.04 (d, J=7.1 Hz, 1H), 3.97 (s, 3H), 1.48 (dd, J=6.5, 1.0 Hz, 3H); ESIMS m/z 249 ([M+H]$^+$).
The following compounds were prepared in accordance to the procedure in Example 29:

Methyl 4-amino-3,5-dichloro-6-(1-hydroxyethyl)picolinate (C30)

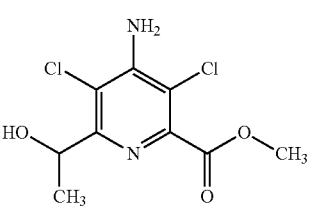

Isolated as white solid: mp 128-130° C.; $^1$H NMR (400 MHz, DMSO-d$_6$) δ 6.90 (s, 2H), 5.07 (d, J=6.3 Hz, 1H), 4.99 (p, J=6.3 Hz, 1H), 3.87 (s, 3H), 1.31 (d, J=6.4 Hz, 3H); ESIMS m/z 263 ([M−H]$^-$).

Methyl
4-amino-3-chloro-6-(1-hydroxyethyl)picolinate
(C31)

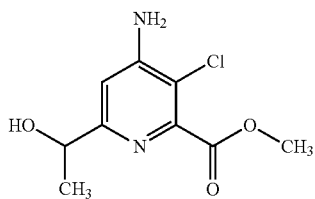

Isolated as a white solid: mp 97-99° C.; $^1$H NMR (400 MHz, CDCl$_3$) δ 6.76 (s, 1H), 4.92-4.67 (m, 3H), 3.98 (s, 3H), 3.52 (d, J=4.7 Hz, 1H), 1.47 (d, J=6.5 Hz, 3H); ESIMS m/z 229 ([M−H]$^−$).

Example 30

Preparation of methyl 4-((tert-butoxycarbonyl)amino)-6-(3,3,3-trifluoropropyl)picolinate (C32)

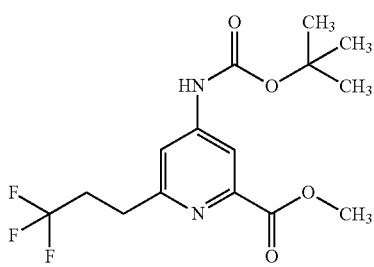 [SMILES: COC(=O)c1cc(NC(=O)OC(C)(C)C)cc(CCC(F)(F)F)n1]

A flask containing (Z)-methyl 4-((tert-butoxycarbonyl)amino)-3-chloro-6-(3,3,3-trifluoroprop-1-en-1-yl)-picolinate (0.10 g, 0.26 mmol) in methanol (1.3 mL) was evacuated and filled with argon three times. Palladium on carbon (10%, 0.010 g, 0.090 mmol) was added, and the flask was evacuated and filled with hydrogen three times. The reaction mixture was stirred at room temperature for 1 hour, then filtered through Celite® and washed with methanol. The filtrate was concentrated to afford the title compound as a light yellow solid: $^1$H NMR (400 MHz, DMSO-d$_6$) δ 10.22 (s, 1H), 8.06 (d, J=1.7 Hz, 1H), 7.64 (s, 1H), 3.87 (s, 3H), 3.03-2.92 (m, 2H), 2.78-2.58 (m, 2H), 1.50 (s, 9H); $^{19}$F NMR (376 MHz, DMSO-d$_6$) δ −64.72; ESIMS m/z 347 ([M−H]$^−$).

Example 31

Preparation of methyl 6-allyl-4-(di-tert-butyloxycarbonyl)amino-3-chloropicolinate (C33)

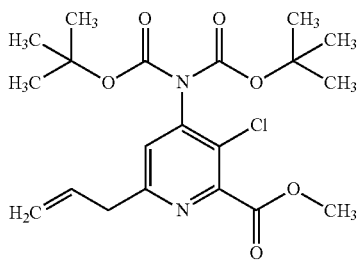 [SMILES: C=CCc1cc(N(C(=O)OC(C)(C)C)C(=O)OC(C)(C)C)c(Cl)c(C(=O)OC)n1]

To a solution of methyl 6-allyl-4-amino-3-chloropicolinate (4.10 g, 18.1 mmol) in 1,2-dichloroethane (75 mL) was added di-tert-butyl dicarbonate (11.8 g, 54.3 mmol) and 4-dimethylaminopyridine (0.370 g, 3.00 mmol) and stirred at room temperature overnight. The reaction mixture was directly adsorbed onto silica gel and purified by flash column chromatography (0-40% ethyl acetate/hexanes) to afford the title compound as a clear oil (5.21 g, 67%): $^1$H NMR (400 MHz, CDCl$_3$) δ 7.19 (s, 1H), 6.13-5.90 (m, 1H), 5.27-5.07 (m, 2H), 4.04-3.95 (m, 3H), 3.69-3.54 (m, 2H), 1.41 (s, 18H); $^{13}$C NMR (101 MHz, CDCl$_3$) δ 164.83, 159.33, 149.32, 148.59, 146.61, 134.42, 126.94, 125.58, 118.00, 84.11, 53.12, 41.83, 27.75; ESIMS m/z 427 ([M+H]$^+$).

The following compounds were prepared in accordance to the procedure in Example 31:

Methyl 6-allyl-4-(di-tert-butyloxycarbonyl)amino-3-chloro5-fluoropicolinate (C34)

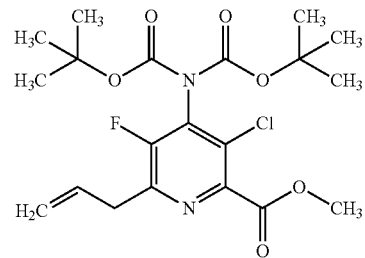 [SMILES: C=CCc1nc(C(=O)OC)c(Cl)c(N(C(=O)OC(C)(C)C)C(=O)OC(C)(C)C)c1F]

Isolated as a clear oil (2.12 g, 88%): $^1$H NMR (300 MHz, CDCl$_3$) δ 5.98 (ddt, J=16.8, 10.2, 6.5 Hz, 1H), 5.21-5.00 (m, 2H), 3.99 (s, 3H), 3.74-3.58 (m, 2H), 1.40 (s, 18H); $^{19}$F NMR (376 MHz, CDCl$_3$) δ −124.95; ESIMS m/z 446 ([M+H]$^+$).

Methyl 4-(di-tert-butyloxycarbonyl)amino-3-chloro-6-(prop-1-en-2-yl)picolinate (C35)

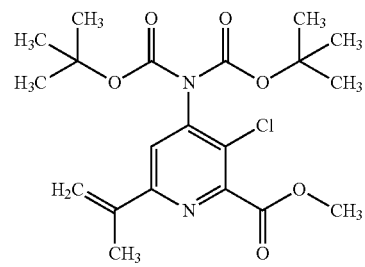 [SMILES: C=C(C)c1cc(N(C(=O)OC(C)(C)C)C(=O)OC(C)(C)C)c(Cl)c(C(=O)OC)n1]

Isolated as a clear oil (1.169 g, 80%): $^1$H NMR (400 MHz, CDCl$_3$) δ 7.42 (s, 1H), 5.93 (s, 1H), 5.45-5.36 (m, 1H), 4.01 (s, 3H), 2.20 (d, J=0.4 Hz, 3H), 1.42 (s, 18H); $^{13}$C NMR (101 MHz, CDCl$_3$) δ 165.05, 157.07, 149.39, 148.48, 146.36, 141.13, 126.97, 122.04, 117.91, 84.11, 52.96, 27.78, 20.16; ESIMS m/z 428 ([M+H]$^+$).

Methyl 4-(di-tert-butyloxycarbonyl)amino-3-chloro-5-fluoro-6-(prop-1-en-2-yl)picolinate (C36)

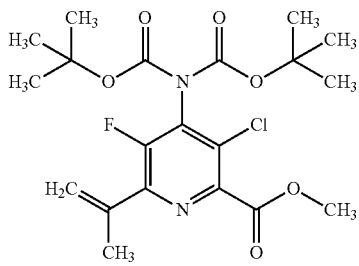 [SMILES: C=C(C)c1nc(C(=O)OC)c(Cl)c(N(C(=O)OC(C)(C)C)C(=O)OC(C)(C)C)c1F]

Isolated as a clear oil (1.80 g, 85%): $^1$H NMR (400 MHz, CDCl$_3$) δ 5.84-5.78 (m, 1H), 5.61 (dt, J=2.5, 1.3 Hz, 1H), 3.99 (s, 3H), 2.23 (d, J=0.8 Hz, 3H), 1.42 (s, 18H); $^{19}$F NMR (376 MHz, CDCl$_3$) δ −121.71; ESIMS m/z 445 ([M+H]$^+$).

Example 32

Preparation of methyl 4-(di-tert-butyloxycarbonyl)amino-3-chloro-6-vinylpicolinate (C37)

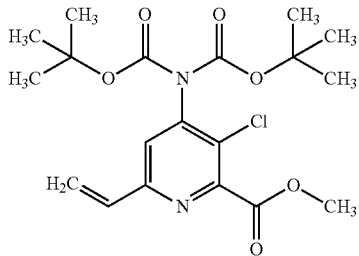

A mixture of methyl 4-amino-3-chloro-6-vinylpicolinate (1.33 g, 6.25 mmol), di-tert-butyl dicarbonate (4.36 mL, 18.8 mmol), and 4-dimethylaminopyridine (0.115 g, 0.940 mmol) in 1,2-dichloroethane (12.5 mL) was stirred at room temperature overnight. The reaction mixture was directly purified by flash column chromatography (0-100% ethyl acetate/hexanes) to afford the title compound as a white solid (1.45 g, 56%): mp 121-122° C.; $^1$H NMR (400 MHz, CDCl$_3$) δ 7.33 (s, 1H), 6.81 (dd, J=17.5, 10.8 Hz, 1H), 6.23 (dd, J=17.5, 0.7 Hz, 1H), 5.61 (dd, J=10.8, 0.7 Hz, 1H), 4.01 (s, 3H), 1.41 (s, 18H); $^{13}$C NMR (101 MHz, CDCl$_3$) δ 164.97, 154.95, 149.46, 149.07, 146.84, 134.95, 127.57, 123.26, 121.00, 84.37, 53.23, 27.92; ESIMS m/z 413 ([M+H]$^+$).

Example 33

Preparation of tributyl(1-fluorovinyl)stannane (C38)

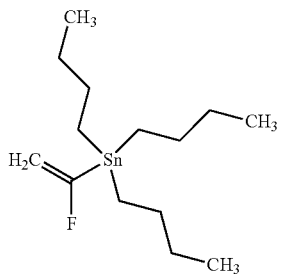

To oven-dried cesium fluoride (0.25 g, 1.7 mmol) in anhydrous dimethylformamide (33 mL) was added bis(tributyltin)oxide (6.1 g, 10 mmol) and (1-fluorovinyl)(methyl)diphenylsilane (4.0 g, 17 mmol). The reaction mixture was sonicated for 3 hours, transferred to a separatory funnel containing water (100 mL) and extracted with hexanes/diethyl ether (3:1, 200 mL). The organic layer was washed with water (75 mL), dried over anhydrous sodium sulfate, filtered, and purified by flash column chromatography (100% hexanes) to afford the title compound as a clear liquid (3.5 g, 63%): $^1$H NMR (400 MHz, CDCl$_3$) δ 5.31 (dd, J=38.3, 2.8 Hz, 1H), 4.56 (dd, J=67.8, 2.8 Hz, 1H), 1.59-1.49 (m, 6H), 1.33 (dq, J=14.4, 7.3 Hz, 6H), 1.05-0.98 (m, 6H), 0.90 (t, J=7.3 Hz, 9H); $^{19}$F NMR (376 MHz, CDCl$_3$) δ −84.90.

Example 34

Preparation of (Z)-methyl 4-((tert-butoxycarbonyl)amino)-3-chloro-6-(3,3,3-trifluoroprop-1-en-1-yl)-picolinate (C39)

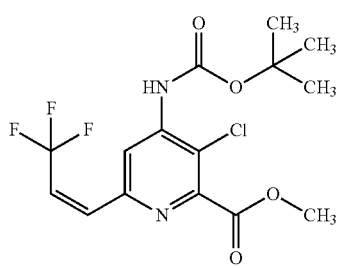 [SMILES: COC(=O)c1nc(/C=C\C(F)(F)F)cc(NC(=O)OC(C)(C)C)c1Cl]

To a 1 M solution of tetrabutylammonium fluoride (14.5 mL, 14.5 mmol) was added 4 Å molecular sieves (14.0 g powder) and stirred overnight at room temperature under argon. To the mixture was added a solution of methyl 4-(di-tert-butyloxycarbonyl)amino-3-chloro-6-formylpicolinate (0.600 g, 1.45 mmol) and diphenyl(2,2,2-trifluoroethyl)phosphine oxide (0.822 g, 2.89 mmol) in tetrahydrofuran (30 mL). The reaction was stirred at room temperature for 2 hours and then filtered through Celite® and washed with ethyl acetate. The filtrate was concentrated and purified by flash column chromatography (0-100% ethyl acetate/hexanes) twice to afford the title compound as a clear oil (0.221 g, 40%): $^1$H NMR (400 MHz, CDCl$_3$) δ 8.50 (s, 1H), 7.39 (s, 1H), 6.95 (d, J=12.6 Hz, 1H), 5.98 (dq, J=12.6, 8.7 Hz, 1H), 4.00 (s, 3H), 1.55 (s, 9H); $^{19}$F NMR (376 MHz, CDCl$_3$) δ −58.01; ESIMS m/z 380 ([M]$^−$).

Example 35

Preparation of methyl 4-amino-3-chloro-6-(1,2-dibromoethyl)picolinate (F34)

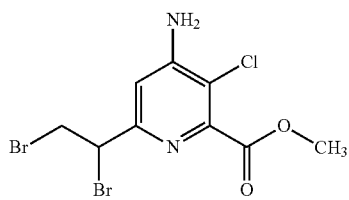 [SMILES: COC(=O)c1nc(C(Br)CBr)cc(N)c1Cl]

Methyl 4-acetamido-3-chloro-6-(1,2-dibromoethyl)picolinate (0.062 g, 0.15 mmol, 1 equiv) was dissolved in methanol (1 mL) and acetyl chloride (0.12 mL, 1.56 mmol) was added slowly (exothermic). The reaction was stirred at room temperature overnight, then concentrated, diluted with methylene chloride, and washed with saturated sodium bicarbonate. The biphasic mixture was extracted with methylene chloride (2×), and the organics were dried over sodium sulfate, filtered, and concentrated to afford the title compound as an off-white oily solid (0.035 g, 63%).

The following compounds were prepared in accordance to the procedure in Example 35:

Methyl 4-amino-6-(2-bromo-1-fluoroethyl)-3-chloropicolinate (F18)

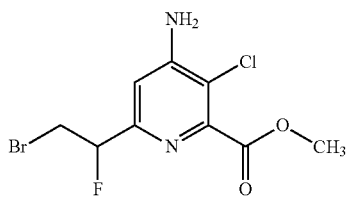

Isolated as a tan solid (0.093 g, 96%).

Example 36

Preparation of methyl 4-amino-3-chloro-6-(1-fluoropropan-2-yl)picolinate (F20)

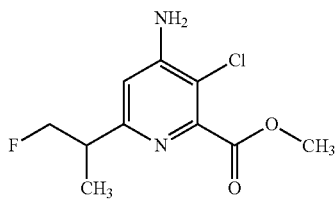 [SMILES: COC(=O)c1nc(C(C)CF)cc(N)c1Cl]

To a solution of methyl 4-(di-tert-butyloxycarbonyl)amino-3-chloro-6-(1-fluoropropan-2-yl)picolinate (0.064 g, 0.14 mmol) in methylene chloride (1 mL) at 0° C. was added trifluoroacetic acid (0.36 mL, 4.7 mmol) and stirred at 0° C. for 1 hour and then at room temperature overnight. The reaction mixture was poured into saturated aqueous sodium bicarbonate and extracted three times with ethyl acetate. The combined organic layer was dried over anhydrous sodium sulfate, filtered, and concentrated. The residue was purified by preparative thin layer chromatography (30% ethyl acetate/hexanes) to afford the title compound as a white solid (0.024 g, 68%).

Example 37

Preparation of methyl 4-amino-6-(3,3,3-trifluoropropyl)picolinate (C40)

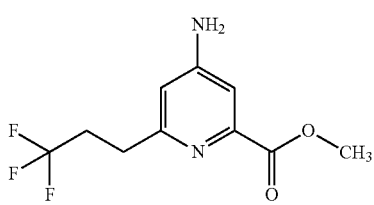 [SMILES: COC(=O)c1cc(N)cc(CCC(F)(F)F)n1]

To a solution of methyl 4-((tert-butoxycarbonyl)amino)-6-(3,3,3-trifluoropropyl)picolinate (0.075 g, 0.22 mmol) in methylene chloride (0.81 mL) was added trifluoroacetic acid (0.27 mL), and the reaction was stirred at room temperature for 2 hours. The reaction mixture was poured into a saturated aqueous sodium bicarbonate solution and extracted three times with ethyl acetate. The organic layers were dried over anhydrous sodium sulfate, filtered, and concentrated to afford the title compound as a yellow solid (0.058 g, 98%): $^1$H NMR (400 MHz, CDCl$_3$/5% MeOD) δ 7.23 (s, 1H), 6.53 (s, 1H), 3.94 (s, 3H), 2.94 (dd, J=9.5, 6.7 Hz, 2H), 2.63-2.45 (m, 2H); $^{19}$F NMR (376 MHz, CDCl$_3$) δ −66.42; ESIMS m/z 248 ([M+H]$^+$).

Example 38

Preparation of methyl 6-acetyl-4-amino-3-chloro-5-fluoropicolinate (C41)

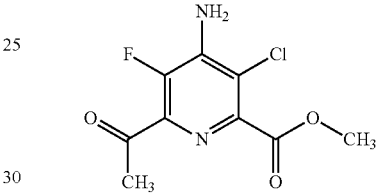

To a solution of methyl 4-amino-3-chloro-6-(1-ethoxyvinyl)-5-fluoropicolinate (1.30 g, 4.73 mmol) in tetrahydrofuran (39 mL) was added 2 N hydrochloric acid (4.70 mL, 9.50 mmol) and stirred at room temperature over the weekend. The solvent was removed under vacuum, and the residue was partitioned between ethyl acetate and water. The organic layer was dried over anhydrous sodium sulfate and concentrated. The crude product was purified by flash column chromatography (2-20% ethyl acetate/methylene chloride) to provide the title compound as an off-white solid (0.990 g, 85%): mp 150-152° C.; $^1$H NMR (400 MHz, CDCl$_3$) δ 4.99 (s, 2H), 4.00 (s, 3H), 2.67 (d, J=0.8 Hz, 3H); $^{19}$F NMR (376 MHz, CDCl$_3$) 6-139.03; ESIMS m/z 247 ([M+H]$^+$).

The following compounds were prepared in accordance to the procedure in Example 38:

Methyl 6-acetyl-4-amino-3,5-dichloropicolinate (C42)

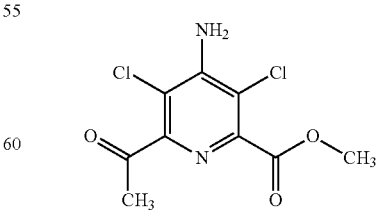

Isolated as an off-white solid (1.23 g, 87%): mp 109-111° C.; $^1$H NMR (400 MHz, CDCl$_3$) δ 5.42 (s, 2H), 4.00 (s, 3H), 2.66 (s, 3H); ESIMS m/z 261 ([M−H]$^−$).

Methyl 6-acetyl-4-amino-3-chloropicolinate (C43)

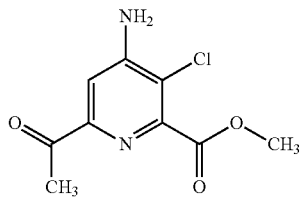

Isolated as a white solid: $^1$H NMR (400 MHz, CDCl$_3$) δ 7.42 (s, 1H), 4.91 (s, 2H), 4.02 (s, 3H), 2.67 (s, 3H); ESIMS m/z 227 ([M−H]$^−$).

Example 39

Preparation of methyl 4-amino-3-chloro-6-(difluoromethyl)picolinate (F27)

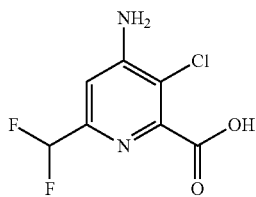 [SMILES: Nc1cc(C(F)F)nc(C(=O)O)c1Cl]

To a solution of methyl 4-amino-3-chloro-6-(difluoromethyl)picolinate (0.14 g, 0.59 mmol) in methanol (6 mL) was added 2 N sodium hydroxide (0.22 mL, 0.60 mmol) and stirred at room temperature for 4 days. The methanol was concentrated off, and the mixture was acidified with 2 N hydrochloric acid. A white precipitate formed and was collected by vacuum filtration to afford the title compound (0.044 g). The aqueous filtrate was purified by reverse-phase flash column chromatography (0-100% acetonitrile/water) to afford an additional amount of the title compound (0.090 g). Both isolations combined afforded the title compound as a white powder (0.134 g, 100%).

The following compounds were prepared in accordance to the procedure in Example 39:

4-Amino-3,5-dichloro-6-(difluoromethyl)picolinic acid (F13)

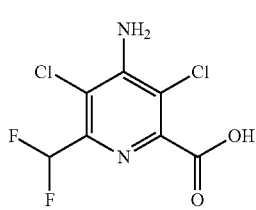 [SMILES: Nc1c(Cl)c(C(=O)O)nc(C(F)F)c1Cl]

Isolated as a white solid (0.082 g, 72%).

4-Amino-3-chloro-5-fluoro-6-(fluoromethyl)picolinic acid (F36)

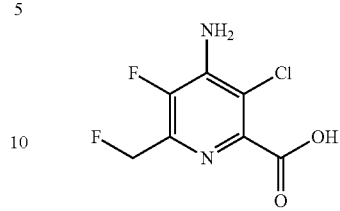

Isolated as an off-white solid (0.066 g, 90%).

4-Amino-3,5-dichloro-6-(fluoromethyl)picolinic acid (F25)

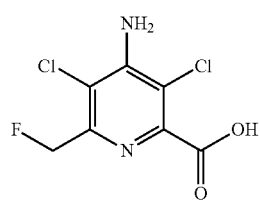 [SMILES: Nc1c(Cl)c(CF)nc(C(=O)O)c1Cl]

Isolated as a white solid (0.060 g, 71%).

4-Amino-3-chloro-6-(1-fluorovinyl)picolinic acid (F23)

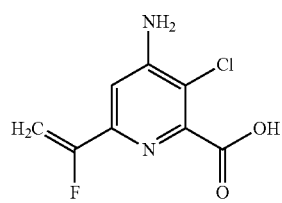

Isolated as a white solid (0.052 g, 45%).

Example 40

Preparation of 4-amino-3-chloro-5-fluoro-6-(1-fluoroethyl)picolinic acid (F30)

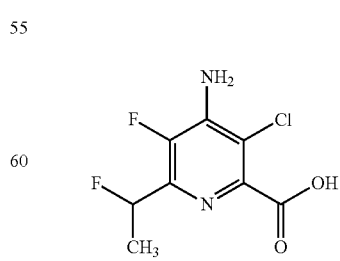

To a solution of methyl 4-amino-3-chloro-5-fluoro-6-(1-fluoroethyl)picolinate (0.187 g, 0.75 mmol) in methanol (14.9 mL) was added 2 N sodium hydroxide (1.49 mL, 3.00 mmol) and stirred at room temperature overnight. The reaction was acidified with 2 N hydrochloric acid and concentrated. The aqueous mixture was extracted twice with ethyl acetate. The organic layers were dried over anhydrous magnesium sulfate, filtered and concentrated to provide the title compound as a yellow solid (0.177 g, 100%).

The following compounds were prepared in accordance to the procedure in Example 40:

4-Amino-3,5-dichloro-6-(1-fluoroethyl)picolinic acid (F16)

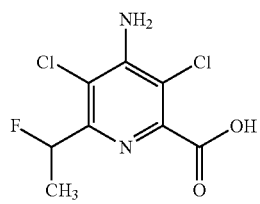

4-Amino-3-chloro-6-(1-fluoroethyl)picolinic acid (F24)

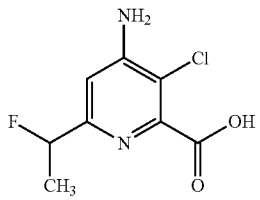

4-Amino-3-chloro-6-(difluoromethyl)-5-fluoropicolinic acid (F32)

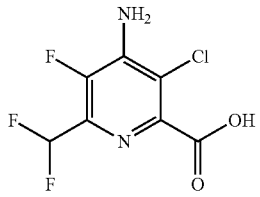 [SMILES: Nc1c(F)c(C(F)F)nc(C(=O)O)c1Cl]

TABLE 1

Compound Number, Structure, Preparation and Appearance

| NO. | Structure | APPEARANCE | PREPARED AS IN EXAMPLE: |
|---|---|---|---|
| F1 | 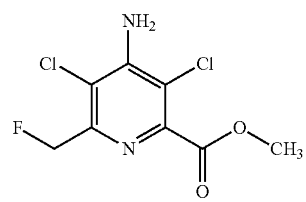 | White Solid | 16 |
| F2 | 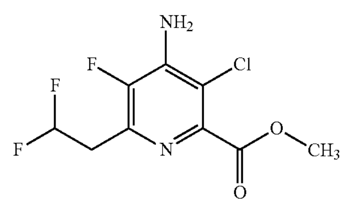 [SMILES: COC(=O)c1nc(CC(F)F)c(F)c(N)c1Cl] | White Solid | 22 |
| F3 | 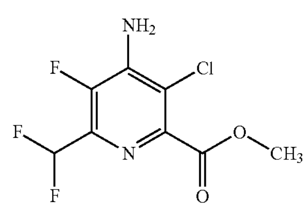 [SMILES: COC(=O)c1nc(C(F)F)c(F)c(N)c1Cl] | White Solid | 24 |
| F5 | 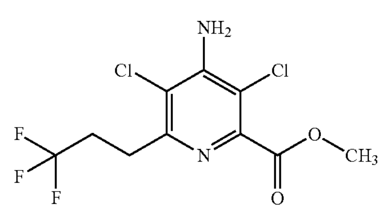 [SMILES: COC(=O)c1nc(CCC(F)(F)F)c(Cl)c(N)c1Cl] | Yellow Solid | 26 |

TABLE 1-continued

Compound Number, Structure, Preparation and Appearance

| NO. | Structure | APPEARANCE | PREPARED AS IN EXAMPLE: |
|---|---|---|---|
| F6 | (structure) | White Powder | 2 |
| F7 | (structure) | White Solid | 15 |
| F8 | (structure) | Yellow Oil | 19 |
| F9 | (structure) | Tan Solid | 19 |
| F10 | (structure) | White Solid | 23 |
| F11 | (structure) | White solid | 18 |
| F12 | (structure) | White Solid | 15 |

TABLE 1-continued

Compound Number, Structure, Preparation and Appearance

| NO. | Structure | APPEARANCE | PREPARED AS IN EXAMPLE: |
|---|---|---|---|
| F13 | 4-amino-3,5-dichloro-6-(difluoromethyl)pyridine-2-carboxylic acid | White Solid | 39 |
| F14 | methyl 4-amino-3-chloro-5-fluoro-6-(fluoromethyl)pyridine-2-carboxylate | White Powder | 16 |
| F15 | methyl 4-amino-3-chloro-5-fluoro-6-(1-fluoroethyl)pyridine-2-carboxylate | White Solid | 23 |
| F16 | 4-amino-3,5-dichloro-6-(1-fluoroethyl)pyridine-2-carboxylic acid | White Solid | 40 |
| F17 | methyl 4-amino-3-chloro-6-(1,2,2-trifluorovinyl)pyridine-2-carboxylate | Yellow Solid | 4 |
| F18 | methyl 4-amino-6-(2-bromo-1-fluoroethyl)-3-chloropyridine-2-carboxylate | Tan Solid | 35 |
| F19 | methyl 4-amino-3-chloro-6-(1-fluoroethyl)pyridine-2-carboxylate | White Solid | 23 |

TABLE 1-continued

Compound Number, Structure, Preparation and Appearance

| NO. | Structure | APPEARANCE | PREPARED AS IN EXAMPLE: |
|---|---|---|---|
| F20 | 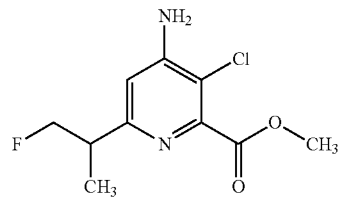 [SMILES: COC(=O)c1nc(C(C)CF)cc(N)c1Cl] | White Solid | 36 |
| F21 | 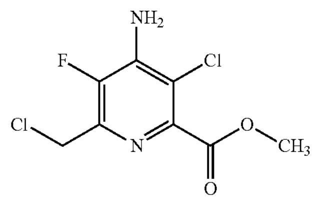 | White Solid | 25 |
| F22 | 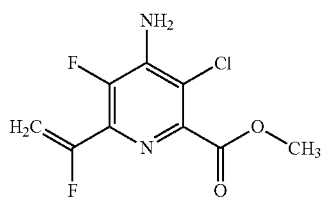 [SMILES: C=C(F)c1nc(C(=O)OC)c(Cl)c(N)c1F] | White Powder | 3 |
| F23 | 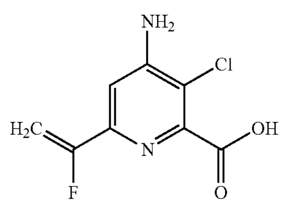 | White Solid | 39 |
| F24 | 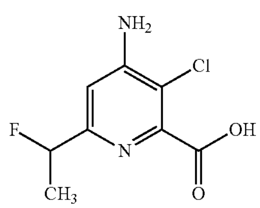 | White Solid | 40 |
| F25 | 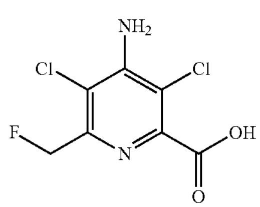 [SMILES: Nc1c(Cl)c(CF)nc(C(=O)O)c1Cl] | White Solid | 39 |
| F26 | 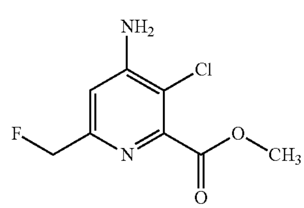 | White Oily Solid | 16 |

TABLE 1-continued

Compound Number, Structure, Preparation and Appearance

| NO. | Structure | APPEARANCE | PREPARED AS IN EXAMPLE: |
|---|---|---|---|
| F27 | 4-amino-3-chloro-6-(difluoromethyl)picolinic acid | White Powder | 39 |
| F28 | methyl 4-amino-3-chloro-6-(1,2-difluoroethyl)picolinate | Clear Oil | 18 |
| F29 | methyl 4-amino-3-chloro-5-fluoro-6-(2-fluoroethyl)picolinate | Yellow Oil | 17 |
| F30 | 4-amino-3-chloro-5-fluoro-6-(1-fluoroethyl)picolinic acid | Low Melting Yellow Solid | 40 |
| F31 | methyl 4-amino-3-chloro-6-(2-fluoroethyl)picolinate | Clear Oil | 17 |
| F32 | 4-amino-3-chloro-6-(difluoromethyl)-5-fluoropicolinic acid | White Solid | 40 |
| F34 | methyl 4-amino-6-(1,2-dibromoethyl)-3-chloropicolinate | Off-White Oily Solid | 35 |

TABLE 1-continued

Compound Number, Structure, Preparation and Appearance

| NO. | Structure | APPEARANCE | PREPARED AS IN EXAMPLE: |
|---|---|---|---|
| F35 | (structure: 4-amino-3-chloro-6-(chloromethyl)pyridine-2-carboxylic acid methyl ester) | Off-White Solid | 25 |
| F36 | (structure: 4-amino-3-chloro-5-fluoro-6-(fluoromethyl)pyridine-2-carboxylic acid) | Off-White Solid | 39 |
| F37 | (structure: 4-amino-3-chloro-5-fluoro-6-(1-fluoropropan-2-yl)pyridine-2-carboxylic acid methyl ester) | White Solid | 21 |

TABLE 2

Analytical Data for Compounds in Table 1

| NO. | IR (cm$^{-1}$) | MASS$^a$ | $^1$H NMR$^b$ | $^{13}$C NMR$^c$; $^{19}$F NMR$^d$ |
|---|---|---|---|---|
| F1 | | m/z 255 ([M + 2H]$^+$) | δ 5.51 (d, J = 47.1 Hz, 2H), 5.31 (s, 2H), 3.99 (s, 3H) | $^{19}$F NMR δ −217.0 |
| F2 | | m/z 269 ([M + H]$^+$) | δ 6.20 (tt, J = 56.2, 4.9 Hz, 1H), 4.87 (s, 2H), 3.98 (s, 3H), 3.36 (tdd, J = 15.9, 4.9, 2.7 Hz, 2H) | $^{19}$F NMR δ −115.96, −115.97, −141.83, −141.84, −141.85 |
| F3 | | EIMS m/z 254 | δ 6.68 (t, J = 56 Hz, 1H), 5.05 (s, 2H), 3.99 (s, 3H); | $^{19}$F NMR δ −116.50, −116.53, −116.65, −116.68, −143.14, −143.17, −143.20 |
| F5 | | m/z 317 ([M]$^+$) | δ 5.20 (s, 2H), 3.98 (s, 3H), 3.19-3.05 (m, 2H), 2.69-2.49 (m, 2H) | $^{19}$F NMR δ −66.58 |
| F6 | | m/z 231 ([M + H]$^+$) | δ 6.95 (d, J = 1.5 Hz, 1H), 5.71 (dd, J = 49.3, 2.9 Hz, 1H), 5.00 (dd, J = 16.6, 2.9 Hz, 1H), 4.84 (s, 2H), 3.99 (s, 3H) | $^{19}$F NMR δ −115.8 |
| F7 | | m/z 270 ([M − H]$^-$) | δ 6.74 (t, J = 53.7 Hz, 1H), 5.42 (s, 2H), 4.00 (s, 3H) | $^{19}$F NMR δ −117.5 |
| F8 | | m/z 265 ([M + H]$^+$) | δ 4.84 (s, 2H), 3.96 (s, 3H), 1.80 (d, J = 0.9 Hz, 3H), 1.74 (d, J = 0.9 Hz, 3H) | |

TABLE 2-continued

Analytical Data for Compounds in Table 1

| NO. | IR (cm$^{-1}$) | MASS$^a$ | $^1$H NMR$^b$ | $^{13}$C NMR$^c$; $^{19}$F NMR$^d$ |
|---|---|---|---|---|
| F9 | | m/z 245 ([M − H]$^−$) | δ 6.96 (d, J = 1.6 Hz, 1H), 4.75 (s, 2H), 3.97 (s, 3H), 1.69 (s, 3H), 1.63 (s, 3H) | $^{19}$F NMR δ −142.9 |
| F10 | | EIMS m/z 266 | δ 5.95 (dq, J = 47.1, 6.5 Hz, 1H), 5.27 (s, 2H), 3.98 (s, 3H), 1.71 (dd, J = 23.9, 6.5 Hz, 3H) | |
| F11 | | EIMS m/z 264 | δ 7.00 (d, J = 1.8 Hz, 1H), 4.85 (s, 2H), 4.68 (dd, J = 47.6, 23.4 Hz, 2H), 3.97 (s, 3H), 1.66 (dd, J = 22.3, 2.1 Hz, 3H) | $^{19}$F NMR δ −161.4, −228.8 |
| F12 | IR (thin film) 3486, 3321, 3202, 3094, 2957, 1714, 1621, 1438, 1340, 1244, 1018 cm$^{-1}$ | m/z 235 ([M − H]$^−$) | δ 7.04 (s, 1H), 6.54 (t, J = 56 Hz, 1H), 4.99 (s, 2H), 4.00 (s, 3H) | $^{19}$F NMR δ −115.8 |
| F13 | | m/z 256 ([M − H]$^−$) | δ 11.01 (s, 1H), 6.81 (t, J = 53.5 Hz, 1H), 5.66 (s, 2H) | $^{19}$F NMR δ −118.9 |
| F14 | | m/z 235 ([M − H]$^−$) | δ 5.54 (d, J = 2.4 Hz, 1H), 5.43 (d, J = 2.4 Hz, 1H), 4.93 (s, 2H), 3.99 (s, 3H) | $^{19}$F NMR δ −141.87, −216.10 |
| F15 | | EIMS m/z 250 | δ 5.82 (dqd, J = 47.0, 6.6, 0.7 Hz, 1H), 4.90 (s, 2H), 3.98 (s, 3H), 1.83-1.65 (m, 3H) | $^{13}$C NMR δ 164.72, 147.28, 144.68, 143.11, 143.06, 142.95, 142.85, 142.75, 142.64, 140.23, 140.11, 116.03, 88.07, 88.06, 86.38, 86.37, 53.03, 19.46, 19.23 |
| F16 | | m/z 251.88 ([M − H]$^−$) | (DMSO-d$_6$) δ 7.00 (s, 2H), 5.94 (dq, J = 47.2, 6.4 Hz, 1H), 1.58 (dd, J = 24.2, 6.4 Hz, 3H) | $^{19}$F NMR (DMSO-d$_6$) δ −170.53 |
| F17 | | m/z 265 ([M − H]$^−$) | δ 6.87 (d, J = 1.5 Hz, 1H), 4.89 (s, 2H), 3.98 (s, 3H) | $^{19}$F NMR δ −93.74, −93.83, −93.87, −93.96, −105.94, −106.07, −106.23, −106.36, −180.32, −180.41, −180.62, −180.70 |
| F18 | | m/z 313 ([M + H]$^+$) | δ 6.92 (dd, J = 1.5, 0.7 Hz, 1H), 5.66 (dddd, J = 47.1, 6.3, 3.0, 0.5 Hz, 1H), 4.92 (s, 2H), 3.98 (s, 3H), 3.92 (ddd, J = 23.2, 11.6, 3.0 Hz, 1H), 3.72 (ddd, J = 24.0, 11.6, 6.3 Hz, 1H) | $^{19}$F NMR δ −187.0 |

TABLE 2-continued

Analytical Data for Compounds in Table 1

| NO. | IR (cm$^{-1}$) | MASS$^a$ | $^1$H NMR$^b$ | $^{13}$C NMR$^c$; $^{19}$F NMR$^d$ |
|---|---|---|---|---|
| F19 | | EIMS m/z 232 | δ 6.90 (d, J = 1.1 Hz, 1H), 5.59 (dq, J = 47.8, 6.5 Hz, 1H), 4.83 (s, 2H), 3.98 (s, 3H), 1.63 (dd, J = 24.6, 6.5 Hz, 3H) | |
| F20 | | m/z 245 ([M − H]$^-$) | δ 6.65 (s, 1H), 4.72 (s, 2H), 4.71-4.43 (m, 2H), 3.97 (s, 3H), 3.27-3.06 (m, 1H), 1.31 (dd, J = 7.1, 0.7 Hz, 3H) | $^{19}$F NMR δ 15.80 |
| F21 | IR (thin film) 3472, 3363, 3198, 1730, 1620 1221 cm$^{-1}$ | m/z 255 ([M + 2H]$^+$) | δ 4.92 (s, 2H), 4.66 (d, J = 2.3 Hz, 2H), 3.98 (s, 3H) | $^{13}$C NMR δ 164.4, 147.6, 145.0, 143.2, 140.9, 140.1, 116.5, 53.1, 40.2; $^{19}$F NMR δ −140.2 |
| F22 | | m/z 249 ([M + H]$^+$) | δ 5.51 (ddd, J = 48.0, 3.4, 0.9 Hz, 1H), 5.24 (ddd, J = 17.3, 3.4, 1.7 Hz, 1H), 4.93 (s, 2H), 3.98 (s, 3H) | $^{19}$F NMR δ −109.3, −138.4 |
| F23 | | m/z 217 ([M + H]$^+$) | (DMSO-d$_6$) δ 6.97 (d, J = 1.8 Hz, 1H), 6.87 (s, 2H), 5.56 (dd, J = 50.8, 3.0 Hz, 1H), 5.06 (dd, J = 17.2, 2.9 Hz, 1H) | $^{19}$F NMR (DMSO-d$_6$) δ −114.9 |
| F24 | | m/z 219.1 ([M + H]$^+$) | (DMSO-d$_6$) δ 6.84 (s, 1H), 6.74 (s, 2H), 5.50 (dq, J = 47.9, 6.6 Hz, 1H), 1.52 (dd, J = 24.6, 6.5 Hz, 3H) | $^{19}$F NMR (DMSO-d$_6$) δ −173.65 |
| F25 | | m/z 238 ([M − H]$^-$) | δ 5.57-5.46 (m, 4H) | $^{19}$F NMR δ 17.7 |
| F26 | | m/z 219 ([M + H]$^+$) | δ 6.88 (dd, J = 1.1, 0.7 Hz, 1H), 5.37 (dd, J = 46.7, 0.7 Hz, 2H), 4.94 (s, 2H), 3.98 (s, 3H) | $^{19}$F NMR δ 14.8 |
| F27 | | m/z 223 ([M + H]$^+$) | (DMSO-d$_6$) δ 7.01-6.63 (m, 4H) | $^{19}$F NMR (DMSO-d$_6$) δ −116.2 |
| F28 | | m/z 251 ([M + H]$^+$) | δ 6.97-6.90 (m, 1H), 5.67 (dddd, J = 47.9, 21.6, 5.5, 1.9 Hz, 1H), 5.02-4.57 (m, 4H), 3.98 (s, 3H) | $^{19}$F NMR δ −195.4, −230.6 |
| F29 | | EIMS m/z 250 | δ 4.79 (m, 4H), 3.97 (s, 3H), 3.20 (dtd, J = 23.7, 6.3, 2.7 Hz, 2H) | $^{13}$C NMR δ 164.89, 148.15, 145.61, 143.14, 143.09, 141.73, 141.67, 141.59, 141.53, 139.59, 139.46, 114.83, 82.53, 80.86, 53.00, 32.31, 32.29, 32.10, 32.08; $^{19}$F NMR δ 18.5, −142.5 |
| F30 | | m/z 237 ([M + H]$^+$) | (DMSO-d6) δ 13.62 (s, 1H), 6.93 (s, 2H), 6.03-5.66 (m, 1H), 1.60 (dd, J = 24.3, 6.5 Hz, 3H) | $^{19}$F NMR (DMSO-d$_6$) δ −143.62, −143.64, −169.83, −169.85 |

TABLE 2-continued

Analytical Data for Compounds in Table 1

| NO. | IR (cm$^{-1}$) | MASS[a] | $^1$H NMR[b] | $^{13}$C NMR[c]; $^{19}$F NMR[d] |
|---|---|---|---|---|
| F31 | | EIMS m/z 232 | δ 6.67 (s, 1H), 4.82-4.68 (m, 4H), 3.98 (s, 3H), 3.05 (dt, J = 26.4, 5.9 Hz, 2H) | $^{19}$F NMR δ −218.0 |
| F32 | | m/z 241.47 ([M + H]$^+$) | (DMSO-d$_6$) δ 7.19 (s, 2H), 7.01 (t, J = 53.1 Hz, 1H) | $^{19}$F NMR (DMSO-d$_6$) δ −117.44, −117.46, −144.46 |
| F34 | | m/z 373 ([M + H]$^+$) | δ 6.81 (s, 1H), 5.07 (dd, J = 10.4, 4.9 Hz, 1H), 4.87 (s, 2H), 4.26 (t, J = 10.2 Hz, 1H), 3.98 (s, 3H), 3.96 (dd, J = 10.0, 4.9 Hz, 1H) | $^{13}$C NMR δ 165.40, 154.89, 150.55, 148.49, 114.23, 109.73, 52.97, 49.27, 33.21 |
| F35 | | m/z 234 ([M − H]$^-$) | δ 6.98 (d, J = 14.4 Hz, 1H), 4.85 (s, 2H), 4.57 (s, 2H), 3.99 (s, 3H) | $^{13}$C NMR δ 165.25, 154.85, 150.86, 147.57, 114.31, 109.66, 53.11, 46.11 |
| F36 | | m/z 223 ([M + H]$^+$) | (DMSO-d$_6$) δ 13.65 (s, 1H), 6.99 (s, 2H), 5.40 (dd, J = 47.6, 2.6 Hz, 2H) | $^{19}$F NMR (DMSO-d$_6$) δ −142.3, −213.5 |
| F37 | | m/z 265 ([M + H]$^+$) | δ 4.77 (s, 2H), 4.71 (dt, J = 47.0, 8.2 Hz, 1H), 4.55 (ddd, J = 47.1, 8.6, 6.7 Hz, 1H), 3.96 (s, 3H), 3.68-3.51 (m, 1H), 1.29 (dd, J = 7.0, 0.9 Hz, 3H) | $^{19}$F NMR δ −144.13, −218.27 |

[a]Mass spectrometry data are electrospray ionization mass spectrometry (ESIMS) unless otherwise noted.
[b]All $^1$H NMR data measured in CDCl$_3$ at 400 MHz unless otherwise noted.
[c]All $^{13}$C NMR data measured in CDCl$_3$ at 101 MHz unless otherwise noted.
[d]All $^{19}$F NMR data measured in CDCl$_3$ at 376 MHz unless otherwise noted.

Examples of General Post-Emergent Herbicidal Activity

A weighed amount, determined by the highest rate to be tested, of each test compound was placed in a 25 mL glass vial and was dissolved in 4 mL of a 97:3 v/v (volume/volume) mixture of acetone and dimethyl sulfoxide to obtain concentrated stock solutions which will be referred to as General Purpose Solvent. If the test compound did not dissolve readily, the mixture was warmed and/or sonicated. The concentrated stock solutions obtained were diluted with 20 mL of an aqueous mixture containing water, General Purpose Solvent, isopropyl alcohol, Atplus 411F crop oil concentrate, and Triton X-155 surfactant in a 46:42:12:1.0:0.02 v/v ratio to obtain spray solutions containing the highest application rates. Additional application rates were obtained by serial dilution of 12 mL of the high rate solution into a solution containing 2 mL of 97:3 v/v (volume/volume) mixture of acetone and dimethyl sulfoxide and 10 mL of an aqueous mixture containing water, General Purpose Solvent, isopropyl alcohol, Atplus 411F crop oil concentrate, and Triton X-155 surfactant in a 46:42:12:1.0:0.02 v/v ratio to obtain 1/2×, 1/4×, 1/8× and 1/16× rates of the high rate. Compound requirements are based upon a 12 mL application volume at a rate of 187 L/ha. Formulated compounds were applied to the plant material with an overhead Mandel track sprayer equipped with a 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by sub-irrigation to prevent wash-off of the test compounds. After 14 days, the condition of the test plants as compared with that of the untreated plants was determined visually and scored on a scale of 0 to 100 percent where 0 corresponds to no injury and 100 corresponds to complete kill.

TABLE A

Visual growth reduction of several plant species via foliar applications.

| | Rate | % Visual Growth Reduction | | | | | | |
|---|---|---|---|---|---|---|---|---|
| Compound | g ai/ha | HELAN | VIOTR | AMARE | CHEAL | EPHHL | ECHCG | ORYSA | ZEAMX |
| F1 | 280 | 100 | 10 | 90 | 90 | 100 | 0 | 0 | 0 |
| F1 | 140 | 100 | 10 | 80 | 90 | 100 | 0 | 0 | 0 |

TABLE A-continued

Visual growth reduction of several plant species via foliar applications.

| Compound | Rate g ai/ha | % Visual Growth Reduction ||||||||
|---|---|---|---|---|---|---|---|---|---|
| | | HELAN | VIOTR | AMARE | CHEAL | EPHHL | ECHCG | ORYSA | ZEAMX |
| F1 | 70 | 100 | 0 | 60 | 90 | 100 | 0 | 0 | 0 |
| F1 | 35 | 100 | 0 | 55 | 90 | 100 | 0 | 0 | 0 |
| F2 | 140 | 80 | 0 | 100 | 90 | 100 | 0 | 0 | 0 |
| F3 | 280 | 90 | 10 | 90 | 100 | 85 | 10 | 0 | 10 |
| F3 | 140 | 90 | 5 | 50 | 100 | 75 | 0 | 0 | 0 |
| F3 | 70 | 90 | 0 | 5 | 100 | 50 | 0 | 0 | 0 |
| F5 | 280 | 60 | 0 | 0 | 0 | 0 | 0 | 0 | 0 |
| F6 | 280 | 20 | 0 | 40 | 90 | 60 | 0 | 0 | 0 |
| F7 | 280 | 90 | 0 | 100 | 0 | 100 | 0 | 0 | 10 |
| F7 | 140 | 80 | 0 | 90 | 0 | 100 | 0 | 0 | 0 |
| F7 | 70 | 60 | 0 | 75 | 0 | 90 | 0 | 0 | 0 |
| F8 | 160 | 90 | 70 | 100 | 90 | 100 | 50 | 8 | 0 |
| F8 | 80 | 90 | 50 | 100 | 90 | 100 | 0 | 0 | 0 |
| F8 | 40 | 90 | 10 | 90 | 90 | 90 | 0 | 0 | 0 |
| F9 | 140 | 50 | 30 | 100 | 85 | 100 | 0 | 0 | 15 |
| F9 | 70 | 50 | 40 | 100 | 70 | 85 | 0 | 0 | 0 |
| F10 | 140 | 100 | 0 | 100 | 85 | 30 | 0 | 0 | 0 |
| F10 | 70 | 85 | 0 | 98 | 85 | 20 | 0 | 0 | 0 |
| F10 | 35 | 80 | 0 | 85 | 80 | 0 | 0 | 0 | 0 |
| F11 | 140 | 70 | 0 | 30 | 0 | 10 | 0 | 0 | 0 |
| F12 | 280 | 100 | 100 | 100 | 100 | 100 | 80 | 8 | 70 |
| F12 | 140 | 100 | 100 | 100 | 100 | 100 | 55 | 0 | 60 |
| F12 | 70 | 100 | 100 | 100 | 100 | 100 | 0 | 0 | 30 |
| F12 | 35 | 100 | 90 | 80 | 90 | 90 | 0 | 0 | 15 |
| F13 | 140 | 85 | 0 | 90 | 90 | 100 | 10 | 0 | 5 |
| F13 | 70 | 75 | 0 | NT* | 90 | 100 | 0 | 0 | 0 |
| F13 | 35 | 60 | 0 | 90 | 90 | 100 | 0 | 0 | 0 |
| F14 | 280 | 95 | 60 | 100 | 100 | 100 | 60 | 0 | 45 |
| F14 | 140 | 95 | 50 | 90 | 100 | 100 | 15 | 0 | 20 |
| F14 | 70 | 90 | 0 | 80 | 90 | 100 | 0 | 0 | 0 |
| F14 | 35 | 85 | 0 | 70 | 85 | 10 | 0 | 0 | 0 |
| F15 | 140 | 100 | 55 | 95 | 80 | 90 | 30 | 0 | 0 |
| F15 | 70 | 90 | 45 | 90 | 85 | 85 | 20 | 0 | 0 |
| F15 | 35 | 80 | 25 | 90 | 80 | 55 | 0 | 0 | 0 |
| F16 | 280 | 100 | 0 | 100 | 100 | 50 | 0 | 0 | 0 |
| F16 | 140 | 90 | 0 | 90 | 100 | 0 | 0 | 0 | 0 |
| F16 | 70 | 80 | 0 | 90 | 100 | 0 | 0 | 0 | 0 |
| F17 | 140 | 60 | 0 | 0 | 0 | 0 | 0 | 0 | 0 |
| F19 | 280 | 80 | 100 | 100 | 100 | 100 | 25 | 0 | 100 |
| F19 | 140 | 50 | 100 | 100 | 100 | 100 | 20 | 0 | 90 |
| F19 | 70 | 20 | 100 | 100 | 100 | 90 | 0 | 0 | 0 |
| F19 | 35 | 10 | 100 | 100 | 100 | 10 | 0 | 0 | 0 |
| F20 | 140 | 50 | 30 | 95 | 80 | 95 | 0 | 0 | 0 |
| F21 | 280 | 0 | 0 | 0 | 0 | 0 | 0 | 0 | 0 |
| F22 | 280 | 80 | 10 | 90 | 90 | 60 | 0 | 0 | 0 |
| F22 | 140 | 80 | 10 | 90 | 90 | 50 | 0 | 0 | 0 |
| F24 | 280 | 80 | 100 | 100 | 100 | 95 | 90 | 10 | 10 |
| F24 | 140 | 75 | 100 | 100 | 100 | 90 | 80 | 0 | 0 |
| F24 | 70 | 65 | 100 | 100 | 100 | 80 | 55 | 0 | 0 |
| F24 | 35 | 50 | 85 | 90 | 100 | 5 | 0 | 0 | 0 |
| F25 | 280 | 90 | 0 | 85 | 80 | 100 | 50 | 0 | 0 |
| F25 | 140 | 80 | 0 | 80 | 80 | 100 | 0 | 0 | 0 |
| F26 | 148 | 90 | 70 | 90 | 90 | 100 | 20 | 0 | 10 |
| F26 | 74 | 90 | 15 | 80 | 90 | 100 | 0 | 0 | 0 |
| F26 | 37 | 70 | 10 | 0 | 90 | 90 | 0 | 0 | 0 |
| F27 | 280 | 100 | NT | 100 | 100 | 100 | 80 | 20 | 60 |
| F27 | 140 | 100 | 100 | 100 | 100 | 100 | 80 | 15 | 60 |
| F27 | 70 | 100 | 100 | 90 | 100 | 100 | 65 | 13 | 50 |
| F27 | 35 | 90 | 80 | 90 | 100 | 90 | 0 | NT | 20 |
| F28 | 280 | 95 | 90 | 100 | 90 | 100 | 0 | 0 | 10 |
| F28 | 140 | 90 | 75 | 100 | 80 | 100 | 0 | 0 | 10 |
| F28 | 70 | 80 | 15 | 80 | 90 | 80 | 0 | 0 | 10 |
| F29 | 280 | 90 | 90 | 100 | 90 | 100 | 60 | 0 | 0 |
| F29 | 140 | 90 | 70 | 100 | 90 | 100 | 10 | 0 | 0 |
| F29 | 70 | 80 | 10 | 90 | 90 | 100 | 0 | 0 | 0 |
| F30 | 280 | 90 | 50 | 100 | 100 | 100 | 80 | 0 | 100 |
| F30 | 140 | 90 | 25 | 100 | 95 | 100 | 65 | 0 | 100 |
| F30 | 70 | 80 | 10 | 100 | 95 | 70 | 0 | 0 | 100 |
| F31 | 180 | 90 | 100 | 15 | 100 | 45 | 0 | 0 | 0 |
| F32 | 280 | 100 | 10 | 85 | 100 | 50 | 60 | 5 | 10 |
| F32 | 140 | 100 | 5 | 55 | 90 | 30 | 55 | 0 | 0 |
| F34 | 264 | 80 | 0 | 0 | 60 | 10 | 0 | 0 | 0 |
| F35 | 280 | 0 | 0 | 0 | 0 | 0 | 0 | 0 | 0 |
| F36 | 280 | 90 | 75 | 100 | 100 | 100 | 95 | 30 | 70 |

TABLE A-continued

Visual growth reduction of several plant species via foliar applications.

| Compound | Rate g ai/ha | % Visual Growth Reduction | | | | | | | |
|---|---|---|---|---|---|---|---|---|---|
| | | HELAN | VIOTR | AMARE | CHEAL | EPHHL | ECHCG | ORYSA | ZEAMX |
| F36 | 140 | 85 | 80 | 100 | 100 | 100 | 80 | 20 | 40 |
| F36 | 70 | 80 | 20 | 100 | 100 | 100 | 50 | 10 | 20 |
| F36 | 35 | 70 | 10 | 100 | 80 | 100 | 50 | 0 | 0 |
| F37 | 132 | 80 | 0 | 50 | 0 | 100 | 0 | 0 | 0 |

*Not tested
HELAN—*Helianthus annuus* L. (sunflower, common)
VIOTR—*Viola tricolor* L. (pansy)
AMARE—*Amaranthus retroflexus* L. (pigweed, redroot)
CHEAL—*Chenopodium album* L. (lambsquarters, common)
EPHHL—*Euphorbia heterophylla* L. (poinsettia, wild)
ECHCG—*Echinochloa crus-galli* (L.) Beauv. (barnyardgrass)
ORYSA—*Oryza sativa* L. (rice)
ZEAMX—*Zea mays* L. (corn)

By applying the well-accepted probit analysis as described by J. Berkson in *Journal of the American Statistical Society*, 48, 565 (1953) and by D. Finney in "Probit Analysis" Cambridge University Press (1952), the dose response data gathered as expressed above can be used to calculate $GR_{20}$, $GR_{50}$ and $GR_{80}$ values, which are defined as growth reduction factors that correspond to the effective dose of herbicide required to kill or control 20 percent, 50 percent or 80 percent, respectively, of a target plant. Data not expressed in Table A may have been used to calculate some of the $GR_{80}$ values in Table B. In some cases, the $GR_{80}$ values may be extrapolations calculated based on the slope of the dose response curve for individual compounds listed in Table B.

TABLE B

Calculated growth reduction values based on 80% visual injury ($GR_{80}$) of treated plants.

| Compound | $GR_{80}$ Value (g ai/ha) | | | | | |
|---|---|---|---|---|---|---|
| | HELAN | VIOTR | AMARE | CHEAL | EPHHL | ECHCG |
| F1 | <17.5 | >280 | 142 | 17.5 | 26.2 | >280 |
| F2 | 80.8 | >140 | 103 | 103 | 114 | >140 |
| F3 | 32.5 | >280 | 112 | <17.5 | 193 | >280 |
| F7 | 145 | >280 | 84.2 | >280 | 17.5 | >280 |
| F8 | 18.6 | 185 | 25.1 | 36.9 | 17.9 | 213 |
| F9 | 237 | >140 | 13.7 | 110 | 49.4 | >140 |
| F10 | 124 | >140 | 18.1 | 23.7 | >140 | >140 |
| F12 | 23.1 | 29.2 | 26.8 | <17.5 | 29.2 | 249 |
| F13 | 85.8 | >140 | 27.6 | 25.1 | 21.7 | >149 |
| F14 | 18 | 334 | 89.2 | 16.8 | 53.9 | 411 |
| F15 | 24.4 | >140 | 22.3 | 48.6 | 75.1 | >140 |
| F16 | 31.4 | >280 | 51.4 | <17.5 | 373 | >280 |
| F19 | 341 | 34.3 | 19.1 | <17.5 | 72.3 | >280 |
| F24 | 199 | 36.7 | 12.3 | <17.5 | 122 | 165 |
| F25 | 146 | >280 | 180 | 176 | <17.5 | 373 |

TABLE B-continued

Calculated growth reduction values based on 80% visual injury ($GR_{80}$) of treated plants.

| Compound | $GR_{80}$ Value (g ai/ha) | | | | | |
|---|---|---|---|---|---|---|
| | HELAN | VIOTR | AMARE | CHEAL | EPHHL | ECHCG |
| F26 | 48.3 | 223 | 104 | 29 | 38.8 | >148 |
| F27 | <17.5 | 59.2 | 17.5 | <17.5 | <17.5 | 187 |
| F28 | 52.9 | 197 | 66.4 | 17.5 | 73 | >280 |
| F29 | 60 | 203 | 55.1 | <17.5 | 53.9 | 432 |
| F30 | 59.3 | >280 | 40.6 | <17.5 | 84.9 | 239 |
| F31 | 42.4 | 74.4 | <17.5 | 6.93 | <17.5 | >180 |
| F32 | 40.8 | >280 | 251 | 26.9 | >280 | 433 |
| F36 | 70 | 246 | <17.5 | 36.1 | <17.5 | 132 |

HELAN—*Helianthus annuus* L. (sunflower, common)
VIOTR—*Viola tricolor* L. (pansy)
AMARE—*Amaranthus retroflexus* L. (pigweed, redroot)
CHEAL—*Chenopodium album* L. (lambsquarters, common)
EPHHL—*Euphorbia heterophylla* L. (poinsettia, wild)
ECHCG—*Echinochloa crus-galli* (L.) Beauv. (barriyardgrass)

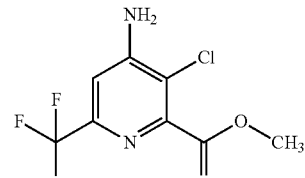

Prior Art 1
(Fields et al. 2001; WO200151468)

TABLE C

Visual growth reduction of several plant species provided by Prior Art 1 via foliar applications.

| Compound | Rate g ai/ha | % Visual Growth Reduction | | | | | | | |
|---|---|---|---|---|---|---|---|---|---|
| | | HELAN | VIOTR | AMARE | CHEAL | EPHHL | ECHCG | ORYSA | ZEAMX |
| Prior Art 1 | 140 | 85 | 95 | 100 | 100 | 95 | 0 | 0 | 0 |
| Prior Art 1 | 70 | 80 | 30 | 80 | 85 | 85 | 0 | 0 | 0 |
| Prior Art 1 | 35 | 70 | 20 | 75 | 80 | 80 | 0 | 0 | 0 |

HELAN—*Helianthus annuus* L. (sunflower, common)
VIOTR—*Viola tricolor* L. (pansy)

TABLE C-continued

Visual growth reduction of several plant species provided by Prior Art 1 via foliar applications.

| | Rate | % Visual Growth Reduction | | | | | | |
|---|---|---|---|---|---|---|---|---|
| Compound | g ai/ha | HELAN | VIOTR | AMARE | CHEAL | EPHHL | ECHCG | ORYSA | ZEAMX |

AMARE—*Amaranthus retroflexus L.* (pigweed, redroot)
CHEAL—*Chenopodium album L.* (lambsquarters, common)
EPHHL—*Euphorbia heterophylla L.* (poinsettia, wild)
ECHCG—*Echinochloa crus-galli (L.) Beauv.* (barnyardgrass)
ORYSA—*Oryza sativa L.* (rice)
ZEAMX—*Zea mays L.* (corn)

TABLE D

Calculated growth reduction values based on 80% visual injury ($GR_{80}$) of plants treated with Prior Art 1.

| | $GR_{80}$ Values (g/ha) | | | | | |
|---|---|---|---|---|---|---|
| Compound | HELAN | VIOTR | AMARE | CHEAL | EPHHL | ECHCG |
| Prior Art 1 | 78.6 | 121 | 29.7 | 32.6 | 26.7 | >140 |

HELAN—*Helianthus annuus L.* (sunflower, common)
VIOTR—*Viola tricolor L.* (pansy)
AMARE—*Amaranthus retroflexus L.* (pigweed, redroot)
CHEAL—*Chenopodium album L.* (lambsquarters, common)
EPHHL—*Euphorbia heterophylla L.* (poinsettia, wild)
ECHCG—*Echinochloa crus-galli (L.) Beauv.* (barnyardgrass)

TABLE F

Calculated growth reduction values based on 80% visual injury ($GR_{80}$) of plants treated with Prior Art 2.

| | $GR_{80}$ Values (g/ha) | | | | | |
|---|---|---|---|---|---|---|
| Compound | HELAN | VIOTR | AMARE | CHEAL | EPHHL | ECHCG |
| Prior Art 1 | 238 | 121 | 36.9 | 47.9 | 31.2 | >140 |

HELAN—*Helianthus annuus L.* (sunflower, common)
VIOTR—*Viola tricolor L.* (pansy)
AMARE—*Amaranthus retroflexus L.* (pigweed, redroot)
CHEAL—*Chenopodium album L.* (lambsquarters, common)
EPHHL—*Euphorbia heterophylla L.* (poinsettia, wild)
ECHCG—*Echinochloa crus-galli (L.) Beauv.* (barnyardgrass)

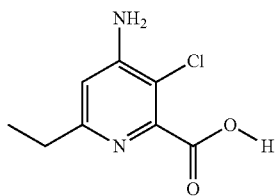

Prior Art 2
(Balko et al. 2004; US20040198608)

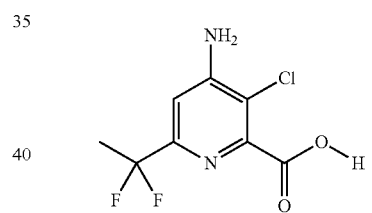

Prior Art 3
(Balko et al. 2005; US20050032651)

TABLE E

Visual growth reduction of several plant species priovided by Prior Art 2 via foliar applications.

| | Rate | % Visual Growth Reduction | | | | | | |
|---|---|---|---|---|---|---|---|---|
| Compound | g ai/ha | HELAN | VIOTR | AMARE | CHEAL | EPHHL | ECHCG | ORYSA | ZEAMX |
| Prior Art 1 | 140 | 50 | 95 | 100 | 95 | 100 | 0 | 0 | 0 |
| Prior Art 1 | 70 | 20 | 90 | 90 | 85 | 85 | 0 | 0 | 0 |
| Prior Art 1 | 35 | 0 | 80 | 75 | 80 | 80 | 0 | 0 | 0 |

HELAN—*Helianthus annuus L.* (sunflower, common)
VIOTR—*Viola tricolor L.* (pansy)
AMARE—*Amaranthus retroflexus L.* (pigweed, redroot)
CHEAL—*Chenopodium album L.* (lambsquarters, common)
EPHHL—*Euphorbia heterophylla L.* (poinsettia, wild)
ECHCG—*Echinochloa crus-galli (L.) Beauv.* (barnyardgrass)
ORYSA —*Oryza sativa L.* (rice)
ZEAMX —*Zea mays L.* (corn)

TABLE G

Visual growth reduction of several plant species provided by Prior Art 3 via foliar applications.

| | Rate | % Visual Growth Reduction | | | | | | |
|---|---|---|---|---|---|---|---|---|
| Compound | g ai/ha | HELAN | VIOTR | AMARE | CHEAL | EPHHL | ECHCG | ORYSA | ZEAMX |
| Prior Art 1 | 140 | 90 | 75 | 100 | 95 | 95 | 0 | 15 | 60 |
| Prior Art 1 | 70 | 80 | 60 | 100 | 90 | 80 | 0 | 10 | 10 |
| Prior Art 1 | 35 | 70 | 30 | 100 | 90 | 70 | 0 | 0 | 0 |

HELAN—*Helianthus annuus L.* (sunflower, common)
VIOTR—*Viola tricolor L.* (pansy)
AMARE—*Amaranthus retroflexus L.* (pigweed, redroot)
CHEAL—*Chenopodium album L.* (lambsquarters, common)
EPHHL—*Euphorbia heterophylla L.* (poinsettia, wild)
ECHCG—*Echinochloa crus-galli (L.) Beauv.* (barnyardgrass)
ORYSA—*Oryza sativa L.* (rice)
ZEAMX—*Zea mays L.* (corn)

TABLE H

Calculated growth reduction values based on 80% visual injury ($GR_{80}$) of plants treated with Prior Art 3.

| | $GR_{80}$ Values (g/ha) | | | | | |
|---|---|---|---|---|---|---|
| Compound | HELAN | VIOTR | AMARE | CHEAL | EPHHL | ECHCG |
| Prior Art 1 | 62.2 | 181 | <8.8 | 14.4 | 67 | >140 |

HELAN—*Helianthus annuus L.* (sunflower, common)
VIOTR—*Viola tricolor L.* (pansy)
AMARE—*Amaranthus retroflexus L.* (pigweed, redroot)
CHEAL—*Chenopodium album L.* (lambsquarters, common)
EPHHL—*Euphorbia heterophylla L.* (poinsettia, wild)
ECHCG—*Echinochloa crus-galli (L.) Beauv.* (barnyardgrass)

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A compound of Formula (I):

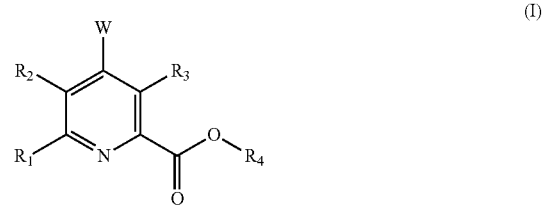

(I)

wherein
$R_1$ is a fluoro substituted $C_1$-$C_4$ alkyl or fluoro substituted $C_2$-$C_4$ alkenyl, with the proviso that $R_1$ is not 1,1-difluoroethyl or trifluoromethyl;
$R_2$ is H, Cl or F;
$R_3$ is halogen;
$R_4$ is H, $C_1$-$C_4$ alkyl or alkylaryl;
W is —$N_3$, —$NR_5R_6$, —NHOH, —$NHCOR_6$ or —N=$CR_7R_8$;
  wherein
  $R_5$ represents H or $C_1$-$C_4$ alkyl;
  $R_6$ represents H, $C_1$-$C_4$ alkyl or $C_1$-$C_4$ alkoxy;
  $R_5$ and $R_6$ taken together with N represent a 5- or 6-membered saturated or unsaturated ring which may contain additional O, S or N heteroatoms;
  $R_7$ represents H or $C_1$-$C_4$ alkyl;
  $R_8$ represents $C_1$-$C_4$ alkoxy or $C_1$-$C_4$ alkylamine;
or a N-oxide or agriculturally acceptable salt thereof.

2. The compound of claim 1, wherein $R_1$ is difluoromethyl.
3. The compound of claim 1, wherein $R_1$ is 1-fluoroethyl.
4. The compound of claim 1, wherein $R_3$ is Cl.
5. The compound of claims 1, wherein $R_4$ is H and W is $NH_2$.
6. The compound of claim 1, wherein $R_4$ is $CH_3$ and W is $NH_2$.
7. The compound of claim 1, wherein $R_1$ is 1-fluoroethyl, $R_2$ is H, and $R_3$ is Cl.
8. The compound of claim 1, wherein $R_1$ is difluoromethyl, $R_2$ is H, and $R_3$ is Cl.
9. A herbicidal composition comprising the compound of claim 1 and one or more agriculturally acceptable adjuvants or carriers.
10. The composition of claim 9, further comprising a herbicide safener.

11. A method of controlling undesirable vegetation which comprises contacting undesirable vegetation or the locus thereof with or applying to the soil or water to prevent the emergence or growth of the undesirable vegetation the compound of claim 1.

12. The method of claim 11, wherein the undesirable vegetation is controlled in glyphosate tolerant crops, glufosinate tolerant crops, dicamba tolerant crops, 2,4-D tolerant crops, ALS tolerant crops, or ACCase tolerant crops.

13. The method of claim 11, wherein the undesirable vegetation is controlled in wheat.

14. The method of claim 11, wherein the undesirable vegetation is controlled in rice.

15. The method of claim 11, wherein the undesirable vegetation is controlled in corn.

16. The method of claim 11, wherein the undesirable vegetation is controlled in pasture grass.

\* \* \* \* \*